(12) United States Patent
Kodama et al.

(10) Patent No.: US 12,147,025 B2
(45) Date of Patent: Nov. 19, 2024

(54) ELECTRONIC MODULE, IMAGE PICKUP UNIT, AND ENDOSCOPE

(71) Applicant: OLYMPUS CORPORATION, Tokyo (JP)

(72) Inventors: Daichi Kodama, Hachioji (JP); Hiroyuki Motohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 75 days.

(21) Appl. No.: 18/078,305

(22) Filed: Dec. 9, 2022

(65) Prior Publication Data

US 2023/0108097 A1 Apr. 6, 2023

Related U.S. Application Data

(63) Continuation of application No. PCT/JP2020/027299, filed on Jul. 13, 2020.

(51) Int. Cl.
*G02B 23/24* (2006.01)
*A61B 1/04* (2006.01)

(52) U.S. Cl.
CPC .......... *G02B 23/2484* (2013.01); *A61B 1/04* (2013.01)

(58) Field of Classification Search
CPC ....... G02B 23/2484; A61B 1/04; A61B 1/051; H05K 1/0284; H05K 3/0011; H05K 3/185; H05K 2201/049; H05K 2201/09118; H05K 2201/0112; H05K 2201/09845

See application file for complete search history.

(56) References Cited

U.S. PATENT DOCUMENTS

| | | | |
|---|---|---|---|
| 5,081,520 A | 1/1992 | Yoshii et al. | |
| 2007/0220744 A1* | 9/2007 | Kitaoka | H05K 3/1258 29/846 |
| 2009/0002973 A1 | 1/2009 | Watanabe et al. | |
| 2014/0240476 A1 | 8/2014 | Satake et al. | |
| 2015/0190039 A1* | 7/2015 | Takahashi | A61B 1/0669 600/109 |

FOREIGN PATENT DOCUMENTS

| | | |
|---|---|---|
| EP | 2 777 481 A1 | 9/2014 |
| JP | 856-144596 A | 11/1981 |

(Continued)

OTHER PUBLICATIONS

International Search Report dated Oct. 13, 2020 received in PCT/JP2020/027299.

*Primary Examiner* — Michael E Teitelbaum
(74) *Attorney, Agent, or Firm* — Scully, Scott, Murphy & Presser, P.C.

(57) ABSTRACT

An electronic module includes: a mount table including a first electrode mounting surface on which an electronic component is mounted; a plurality of electrode mount parts that are formed in the mount table and at which lands corresponding to a plurality of respective electrodes of the electronic component are formed on the first electrode mounting surface; a step part located between the plurality of electrode mount parts and including a predetermined step relative to the first electrode mounting surface of the mount table; and a solder withdrawing part at which an end part of a corresponding one of the lands is extended to the step part or a side surface of the mount table.

20 Claims, 19 Drawing Sheets

(56) References Cited

FOREIGN PATENT DOCUMENTS

| | | |
|---|---|---|
| JP | H04-10447 A | 1/1992 |
| JP | H10-51116 A | 2/1998 |
| JP | 2005-085854 A | 3/2005 |
| JP | 2008-159942 A | 7/2008 |
| JP | 2009-054896 A | 3/2009 |
| JP | 2011-134777 A | 7/2011 |
| JP | 2012-028623 A | 2/2012 |
| JP | 2013-099477 A | 5/2013 |
| JP | 2016-086068 A | 5/2016 |
| WO | 2007/058096 A1 | 5/2007 |
| WO | 2013/069335 A1 | 5/2013 |

\* cited by examiner

ELECTRONIC MODULE, IMAGE PICKUP UNIT, AND ENDOSCOPE

CROSS REFERENCE TO RELATED APPLICATION

This application is a continuation application of PCT/JP2020/027299 filed on Jul. 13, 2020, the entire contents of which are incorporated herein by this reference.

BACKGROUND OF THE INVENTION

1. Field of the Invention

The present invention relates to an electronic module that is preferable for a three-dimensional circuit substrate, an image pickup unit, and an endoscope.

2. Description of the Related Art

In recent years, size reduction of electronic components has been acceleratingly achieved along with spread of portable terminals, and disclosures have been actively made for technologies of achieving size reduction while providing a predetermined function to a substrate (molded component) on which such electronic components are mounted. For example, in a technology of achieving size reduction, which is disclosed as a technology used for an image pickup apparatus in Japanese Patent Application Laid-Open Publication No. 2016-86068, a base portion and a wiring pattern formed on the outer surface of the base portion are provided, a concave portion is formed on a mounting surface, and a substrate has a reflector function of a light-emitting element. In Japanese Patent Application Laid-Open Publication No. 2016-86068, a planar circuit board is mounted in contact on a bottom part of a concave portion of a three-dimensional circuit substrate (molded component) to form a closed space and ensure a component mounting space. A molded component serving as the substrate is formed by what is called a molded-interconnect-devices (MID) technology.

Japanese Patent Application Laid-Open Publication No. 2009-54896 discloses a technology of preventing short-circuit between LED chips with a reduced interval between adjacent LED chips to achieve size reduction of an electronic component (light-emitting device). In the disclosure, a groove portion is formed between substrate mount parts on which LEDs are mounted, and a material having solder wettability is used for the inner surface of the groove portion. With this configuration, contact between solders for mounting chips is prevented, and the chip interval is reduced to achieve size reduction of the light-emitting device.

SUMMARY OF THE INVENTION

An electronic module according to an aspect of the present invention includes: a mount table including a first electrode mounting surface on which an electronic component is mounted; a plurality of electrode mount parts that are formed in the mount table and at which lands corresponding to a plurality of respective electrodes of the electronic component are formed on the first electrode mounting surface; a step part located between the plurality of electrode mount parts and including a predetermined step relative to the first electrode mounting surface of the mount table; and a solder withdrawing part at which an end part of a corresponding one of the lands is extended to the step part or a side surface of the mount table.

An image pickup unit according to an aspect of the present invention includes: an image pickup device; a mount table including a first electrode mounting surface on which the image pickup device is mounted; a plurality of electrode mount parts that are formed in the mount table and at which lands corresponding to a plurality of respective electrodes of the image pickup device are formed on the first electrode mounting surface; a step part located between the plurality of electrode mount parts and including a predetermined step relative to the first electrode mounting surface of the mount table; and a solder withdrawing part at which an end part of a corresponding one of the lands is extended to the step part or a side surface of the mount table.

An endoscope according to an aspect of the present invention includes: an insertion portion; an electronic module provided at the insertion portion; and an image pickup module constituted by an image pickup device and an optical system, the electronic module including: a mount table including a first electrode mounting surface on which the image pickup device is mounted; a plurality of electrode mount parts that are formed in the mount table and at which lands corresponding to a plurality of respective electrodes of the image pickup device are formed on the first electrode mounting surface; a step part located between the plurality of electrode mount parts and including a predetermined step relative to the first electrode mounting surface of the mount table; and a solder withdrawing part at which an end part of a corresponding one of the lands is extended to the step part or a side surface of the mount table.

DETAILED DESCRIPTION OF THE PREFERRED EMBODIMENTS

Embodiments of the present invention will be described below in detail with reference to the accompanying drawings.

First Embodiment

Figure 1:
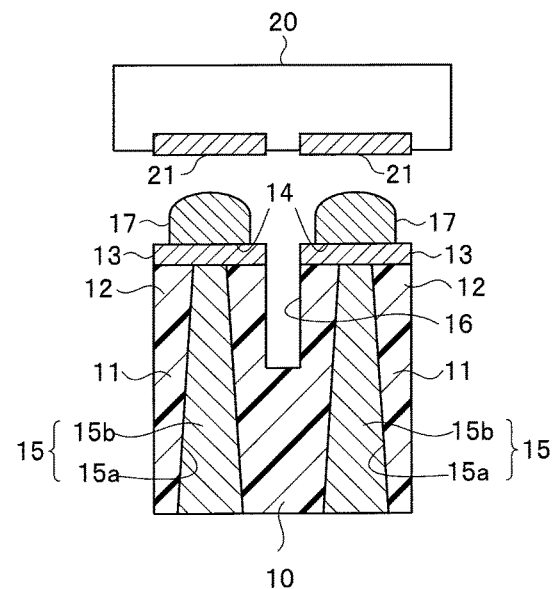
FIG. 1 is a cross-sectional view for description of the configuration of an electronic module according to a first embodiment of the present invention.

FIG. 1 is a cross-sectional view for description of the configuration of an electronic module according to a first embodiment of the present invention.

Note that, in a drawing used in description below, a scale is changed for each constituent component in some cases to set a size in which the constituent component is recognizable in the drawing. The invention is not limited to the number of constituent components illustrated in the drawings, shapes of the constituent components, size ratios of the constituent components, and relative positional relations among the constituent components.

In the present embodiment, a step part is provided between a plurality of electrode mown parts to which a plurality of respective electrodes of an electronic component mounted on a mount part are attached by solder, and thus it is possible to relatively narrow the interval between the electrode mount parts while preventing short-circuit of solder, thereby achieving device size reduction.

Note that the electronic module in FIG. 1 may be configured by, for example, an MID technology. A minute composite fabrication technology disclosed in Japanese Patent Application Laid-Open Publication No. 2008-159942 and Japanese Patent Application Laid-Open Publication No. 2011-134777, in particular, may be used as MID. According to the minute composite fabrication technology, it is possible to achieve what is called a 3D mounting device capable of performing minute patterning and bare chip mounting by using a molding surface activation processing technology, a laser patterning technique, or the like for the MID technology of forming an electric circuit on the surface of an injection mold product.

In FIG. 1, a mount part 10 has a three-dimensional structure in a predetermined shape. An electronic component 20 has a plurality of electrodes 21 on its bottom surface and the electronic component 20 is mounted on the mount part 10 through the electrodes 21. Note that FIG. 1 illustrates a state before the electronic component 20 is mounted on the mount part 10.

In the example illustrated in FIG. 1, the mount part 10 has a substantially rectangular parallelepiped shape and includes a mount table 11 made of resin or the like as a non-conductive member. The mount table 11 may be a molded product shaped by the MID technology and having a wiring function and a mounting function, may be a component formed by a 3D printer or the like, or may be a printed substrate.

A plurality of electrode mount parts 12 corresponding to the plurality of respective electrodes 21 of the mounted electronic component 20 are formed in the mount table 11. Land formation regions are provided for the respective electrode mount parts 12 on an upper surface of the mount table 11, and lands 13 are formed in the land formation regions by plating, for example. Solder 17 is provided on the land 13 of each electrode mount part 12. At mounting, each electrode 21 of the electronic component 20 is soldered by the solder 17 of the corresponding land 13 and electrically connected to the corresponding land 13.

For example, the lands 13 may be formed applying a molding surface activation processing technology to the land formation regions on the upper surface of the mount table 11. When the molding surface activation processing technology is applied, metal cores are formed (activated) through a physicochemical reaction on the surface of resin at the upper surface of the mount table 11, and the resin surface becomes an uneven (roughed) surface that plating is likely to closely contact. After the application of the molding surface activation processing technology, the land formation regions are provided with plating processing to form the lands 13. Note that, in FIG. 1, the lands 13 are formed on the entire surface of the mount table 11, but the lands 13 are formed only in the land formation regions on the surface of the mount table 11 and are not necessarily formed on the entire surface of the mount table 11.

Note that, for sake of simplicity, a direction orthogonal to the upper surface of the mount table 11 is referred to as a height direction of the mount part 10, and in the mount part 10, the lands 13 side of the mount table 11 is referred to as a front side, and a bottom surface side of the mount table 11 opposite to the lands 13 is referred to as a back side.

In the height direction, the height of each land 13 and the height of the upper surface of the mount table 11 other than the land formation regions have a slight height difference in some cases, but the height difference is negligibly small, and the following description assumes that the height of the upper surface of the mount table 11 except for the land formation regions and the height of each land 13 are identical. The upper surface of the mount table (≈upper surface of each land 13) forms a first electrode mounting surface 14 on which the electronic component 20 is mounted.

A via hole opening 15a penetrating from the upper surface of the mount table 11 to the bottom surface thereof is formed in the land formation region of each electrode mount part 12. A film of hole plating 15b is formed in the via hole opening 15a, and accordingly, a via hole 15 is formed. The via hole 15 provided at the electrode mount part 12 has an upper end electrically connected to the corresponding land 13 and has a lower end connected to a non-illustrated wire. With this configuration, at mounting, each electrode 21 of the electronic component 20 is connected to the wire on the bottom surface of the mount table 11 through the corresponding solder 17, the corresponding land 13, and the corresponding via hole 15.

In the mount table 11 according to the present embodiment, a step part 16 having a predetermined height from the front side is formed between the electrode mount parts 12. For example, the step part 16 may be formed by providing a groove on the front side of the mount table 11. Alternatively, for example, the step part 16 may be formed by providing each electrode mount part 12 as a protrusion of a predetermined height toward the front side. Alternatively, for example, the step part 16 may be formed by providing a through-hole at the mount table 11 between the electrode mount parts 12.

The solder 17 provided on each land 13 overflows between the corresponding electrode 21 of the electronic component 20 and the land 13 at soldering of the electrode 21. It is thought that the overflowing solder 17 flows from the land 13 along the surface of the mount table 11 at the step part 16 in accordance with its wettability. In other words, the step part 16 has a function to guide the solder overflowing between the electrode 21 and the land 13 at soldering with a direction change from a direction parallel to the land 13 to the height direction.

Note that the surface of the mount table 11 at the step part 16 may be provided with surface fabrication to improve solder wettability.

Although only two electrode mount parts 12 are illustrated in FIG. 1, the number of electrode mount parts 12 may be equal to or larger than three.

Figure 2:
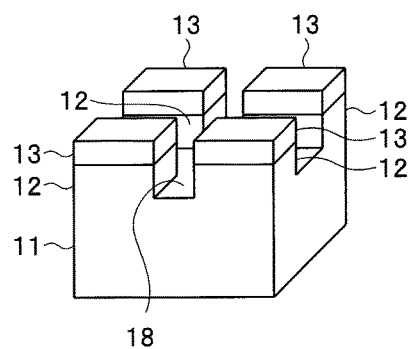
FIG. 2 is a perspective view illustrating an example of a step part.

FIG. 2 is a perspective view illustrating an example of the step part. In FIG. 2, the same constituent component as in FIG. 1 is denoted by the same reference sign, and description thereof will be omitted.

In the example illustrated in FIG. 2, the mount table 11 is provided with four electrode mount parts 12. Lands 13 are formed at the upper ends of the electrode mount parts 12, and four electrodes of a non-illustrated electronic component are soldered to the respective lands 13 at four places so that the electronic component is mounted. A step part 18 as a groove is formed among the electrode mount parts 12. Specifically, the step part 18 is formed in a cross shape when viewed from above the upper surface of the mount table 11.

Figure 3:
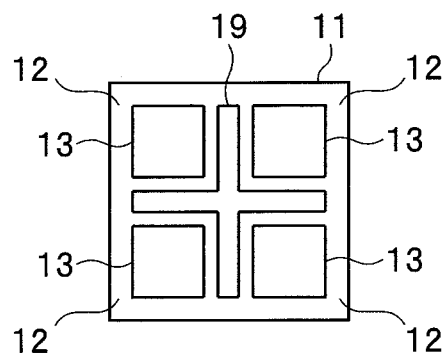
FIG. 3 is a plan view illustrating another example of the step part.

FIG. 3 is a plan view illustrating another example of the step part. In FIG. 3, the same constituent component as in FIG. 1 is denoted by the same reference sign, and description thereof will be omitted.

In the example illustrated in FIG. 3, the mount table 11 is provided with four electrode mount parts 12. The lands 13 are formed at the upper ends of the electrode mount parts 12, and four electrodes of a non-illustrated electronic component are soldered to the respective lands 13 at four places so that the electronic component is mounted. Among the electrode mount parts 12, a step part 19 as a through-hole penetrating the mount table 11 in the height direction is formed. The step part 19 is formed in a cross shape when viewed from above the upper surface of the mount table 11.

Each above-described step part has a function to achieve such an effect of the present embodiment that the interval between the electrode mount parts 12 is relatively narrowed to achieve device size reduction while short-circuit of solder is prevented. The above-described step parts 16, 18, and 19 each have the same function, and the following description is made only on the step part 16 but the same effect is obtained when the other step parts are employed.

Figure 4:
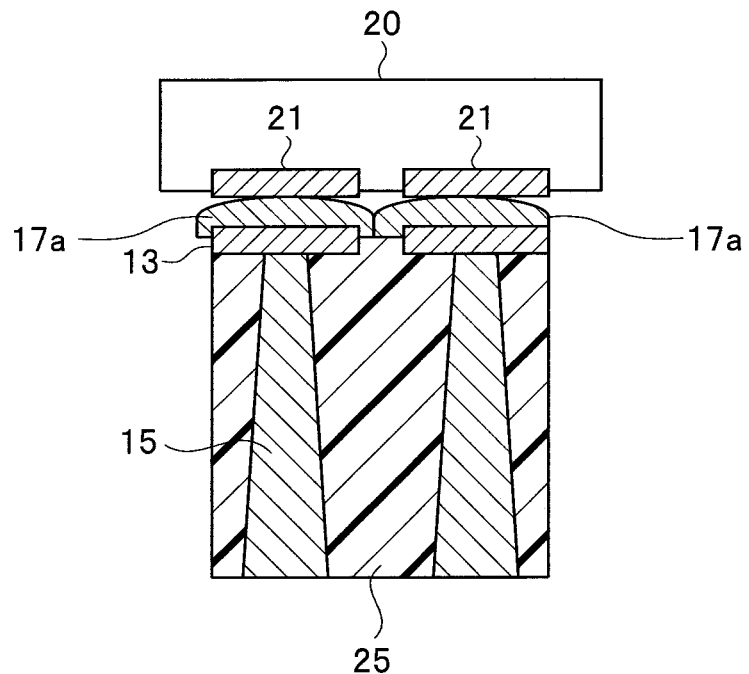
FIG. 4 is an explanatory diagram illustrating a comparative example.
Figure 5:
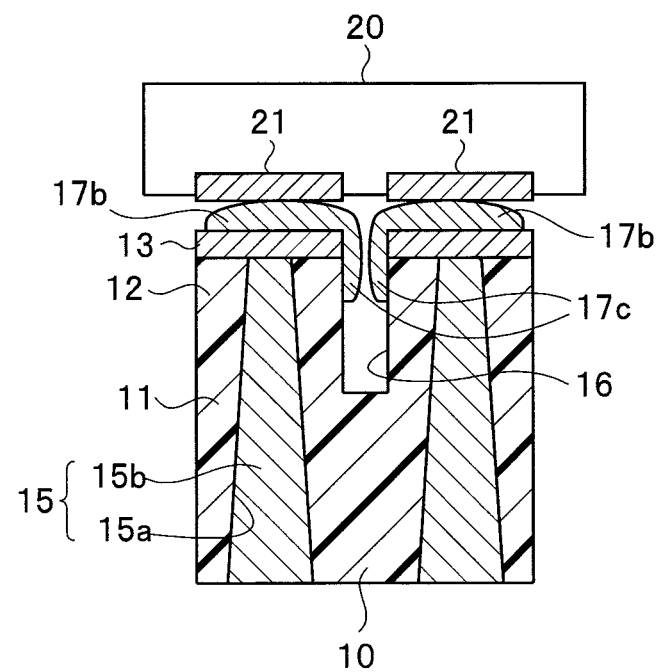
FIG. 5 is an explanatory diagram for description of effects of the present embodiment.

Subsequently, effects of the embodiment thus configured will be described below with reference to FIGS. 4 and 5. FIG. 4 is an explanatory diagram illustrating a comparative example, and FIG. 5 is an explanatory diagram for description of effects of the present embodiment. FIGS. 4 and 5 illustrate a state in which the electronic component 20 is mounted.

FIG. 4 illustrates, for comparison, a mount table 25 configured as the mount table 11 in FIG. 1 from which the step part 16 is omitted. The lands 13 corresponding to the plurality of respective electrodes 21 of the electronic component 20 are provided on an upper surface of the mount table 25, and solder 17a is provided on the lands 13.

At soldering, the electrodes 21 of the electronic component 20 are pressed to the solder 17a and soldered. The solder 17a melts and solder overflowing between each electrode 21 and the corresponding land 13 flows along the upper surface of the mount table 25. When the interval between the lands 13 adjacent to each other is relatively narrow, as illustrated in FIG. 4, the solder 17a overflowing between each electrode 21 and the corresponding land 13 flows on the upper surface of the mount table 25 until the solder 17a contacts the other solder 17a. As a result, short-circuit occurs between the electrodes 21 adjacent to each other.

FIG. 5 illustrates a state in which the electronic component 20 is mounted in the present embodiment. At soldering, when the electrodes 21 of the electronic component 20 are pressed to solder 17b and soldered, the solder 17b melts and protrudes from each land 13, and accordingly, a solder protruding part 17c is formed, Since the step part 16 is formed between the lands 13 adjacent to each other, solder (the solder protruding part 17c) overflowing between each of the corresponding electrodes 21 and the corresponding land 13 flows along the surface of the mount table 11 at the step part 16. In other words, due to the step part 16, the solder protruding part 17c flows with a direction change from a direction parallel to the upper surface of the land 13 to a direction (the height direction) perpendicular to the land 13. Finally, the solder protruding part 17c is formed at the step part 16.

As a result, even when the interval between the lands 13 adjacent to each other is relatively narrow, the solder protruding part 17c overflowing between each electrode 21 and the corresponding land 13 flows to the step part 16 as illustrated in FIG. 5 and the solder protruding parts 17c protruding from the lands 13 adjacent to each other do not contact each other. As a result, occurrence of short-circuit between the electrodes 21 adjacent to each other can be prevented.

Note that since the step part 19 is formed as a through-hole in the example illustrated in FIG. 3, the existence of short-circuit due to flowing solder can be visually checked from the back surface side of the mount table 11, which is another advantage.

In this manner, in the present embodiment, since a step part is formed between a plurality of electrode mount parts to which respective electrodes of an electronic component are soldered, it is possible to reduce a risk that melted solder flows and forms short-circuit with an adjacent electrode. Accordingly, it is possible to shorten the interval between the electrode mount parts while preventing short-circuit, thereby achieving device size reduction.

(Modification)

Figure 6:
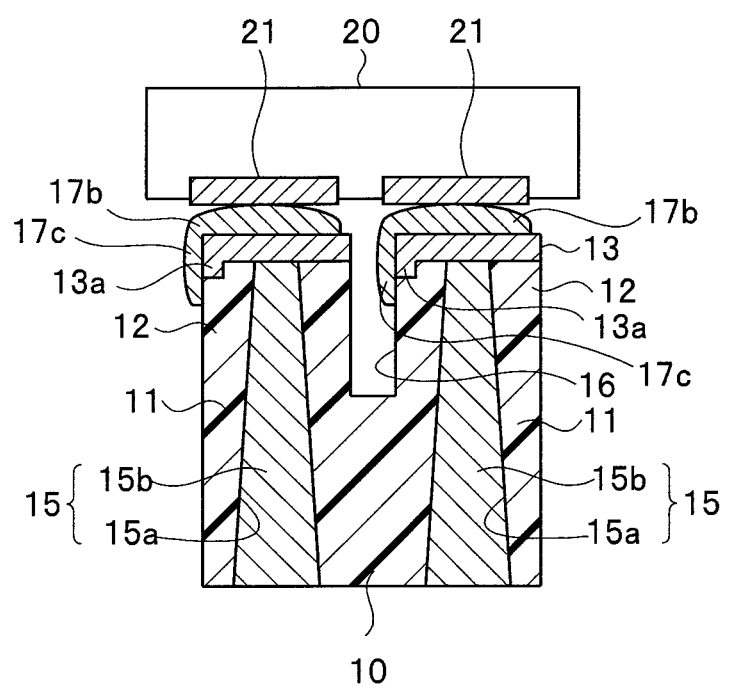
FIG. 6 is a cross-sectional view illustrating a modification.

FIG. 6 is a cross-sectional view illustrating a modification. In FIG. 6, the same constituent component as in FIG. 1 is denoted by the same reference sign, and description thereof will be omitted. Note that FIG. 6 illustrates a state in which the electronic component 20 is mounted.

The modification in FIG. 6 is different from FIG. 1 in that a solder withdrawing part 13a at which each land 13 is extended to the surface of the mount table 11 at the step part 16 or a side surface of the mount table 11 is provided. The solder withdrawing part 13a can provide improved wettability than the surface of the mount table 11.

In the modification as well, at soldering, when the electrodes 21 of the electronic component 20 are pressed to the solder 17b and soldered, the solder 17b melts and protrudes from each land 13, and accordingly, the solder protruding part 17c is formed. Each land 13 is extended to and the solder withdrawing part 13a is formed at the step part 16 between the lands 13 adjacent to each other or the side surface of the mount table 11, and the solder protruding part 17c overflowing from between the corresponding electrode 21 and the land 13 flows along the solder withdrawing part 13a. Wettability is improved by the solder withdrawing part 13a, and the solder protruding part 17c is more reliably guided to the step part 16 or the side surface of the mount table 11.

In a pair of the solder withdrawing parts 13a corresponding to the lands 13 adjacent to each other, one of the solder withdrawing parts 13a is formed on a wall surface of the step part 16 and the other solder withdrawing part 13a is formed on the side surface of the mount table 11. Thus, not both of the solder protruding parts 17c due to solder flowing from the respective lands 13 adjacent to each other are formed in the step part 16, and thus short-circuit can be further prevented. Note that, from a viewpoint of wettability improvement, some effects are obtained even when the solder withdrawing parts 13a connected to the lands 13 adjacent to each other are formed on the wall surface of the same step part 16.

The other effects are the same as those of the embodiment in FIG. 1.

Second Embodiment

Figure 7:
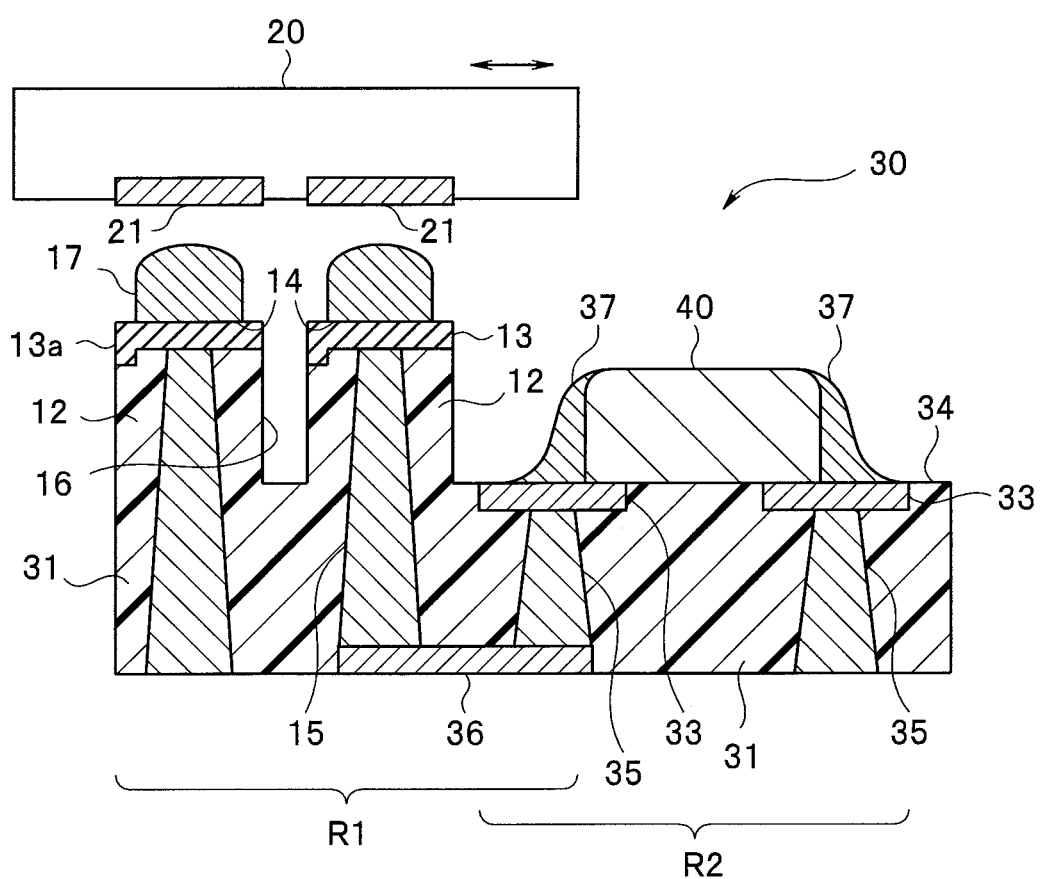
FIG. 7 is a cross-sectional view illustrating a second embodiment of the present invention.

FIG. 7 is a cross-sectional view illustrating a second embodiment of the present invention. In FIG. 7, the same constituent component as in FIG. 6 is denoted by the same reference sign, and description thereof will be omitted. The present embodiment reduces increase of the area of a mount part when not only the electronic component 20 but also another component is mounted.

In FIG. 7, a mount part 30 has a three-dimensional structure in a predetermined shape. The electronic component 20 and a chip component 40 are mounted on the mount part 30. Note that, in FIG. 7, a state before mounting is illustrated for the electronic component 20.

In the example illustrated in FIG. 7, the mount part 30 includes a mount table 31 having the first electrode mounting surface 14 and a second electrode mounting surface 34. The mount table 31 is made of resin or the like as a non-conductive member. The electronic component 20 is mounted on the first electrode mounting surface 14, and the chip component 40 is mounted on the second electrode mounting surface 34. The configuration of a part at which the electronic component 20 is mounted in the mount part 30 is the same as in FIG. 6, and description thereof is omitted.

The chip component 40 may be a bypass capacitor or the like. The bypass capacitor has a function to absorb noise between power sources and achieves a higher noise absorption effect when disposed near the electronic component 20. In the example illustrated in FIG. 7, the bypass capacitor is disposed on the mount table 31 relatively near the electronic component 20.

Note that the following description assumes that four electrode mount parts 12 are formed at the mount part 30, but the number of electrode mount parts 12 may be set as appropriate in accordance with the number of electrodes of a mounted electronic component.

As for a plane parallel to the first electrode mounting surface 14 in FIG. 7, the electronic component 20 occupies a region that is wider in the direction of arrows than a part of the mount part 30 at which the electronic component 20 is mounted. The region in which the electronic component 20 is disposed on the mount part 30 is referred to as a region R1.

The chip component 40 is mounted by using the remaining region of the mount part 30 in which the electronic component 20 is not mounted. Land formation regions for mounting the chip component 40 are provided on an upper surface of the mount table 31, and lands 33 are formed in the land formation regions, for example, by plating. Solder 37 is provided on the land 33. At mounting, the chip component 40 is soldered by the solder 37 on each land 33 and electrically connected to the land 33. Note that the upper surface of the mount table 31 is referred to as the second electrode mounting surface 34. Note that a plane region necessary for mounting of the chip component 40 is referred to as a region R2.

Note that, for sake of simplicity, a direction orthogonal to t upper surface of the mount table 31 is referred to as the height direction of the mount part 30, and in the mount part 30, the lands 13 and 33 side of the mount table 31 is referred to as the front side, and the bottom surface side of the mount table 31 opposite to the lands 13 and 33 is referred to as the back side.

A via hole opening penetrating from the upper surface of the mount table 31 to a bottom surface thereof is formed in the land formation region of each land 33, and a hole plating film is firmed in the via hole opening, and accordingly, a via hole 35 is formed. The via hole 35 has an upper end electrically connected to the corresponding land 33 and has a lower end connected to a wiring pattern 36 and another wiring pattern (not illustrated). With this configuration, at mounting, an electrode of the chip component 40 is connected to the wiring patterns on the bottom surface of the mount table 11 through the solder 37, the land 33, and the via hole 35.

In the present embodiment, the first electrode mounting surface 14 on which the electronic component 20 is mounted and the second electrode mounting surface 34 on which the chip component 40 is mounted have heights different from each other, and the height difference between the surfaces is set to be equal to or larger than the difference between the height of the chip component 40 and the height of the solder 17b after melting (refer to FIG. 6). Specifically, in this case, the position of an upper surface of the chip component 40 in the height direction after mounting is lower than the position of a bottom surface of the electronic component 20 in the height direction after mounting. Thus, the chip component 40 and the electronic component 20 can be disposed in an overlapping manner in the direction of arrows in FIG. 7, which is parallel to the upper surface of the mount table 31.

Figure 8:
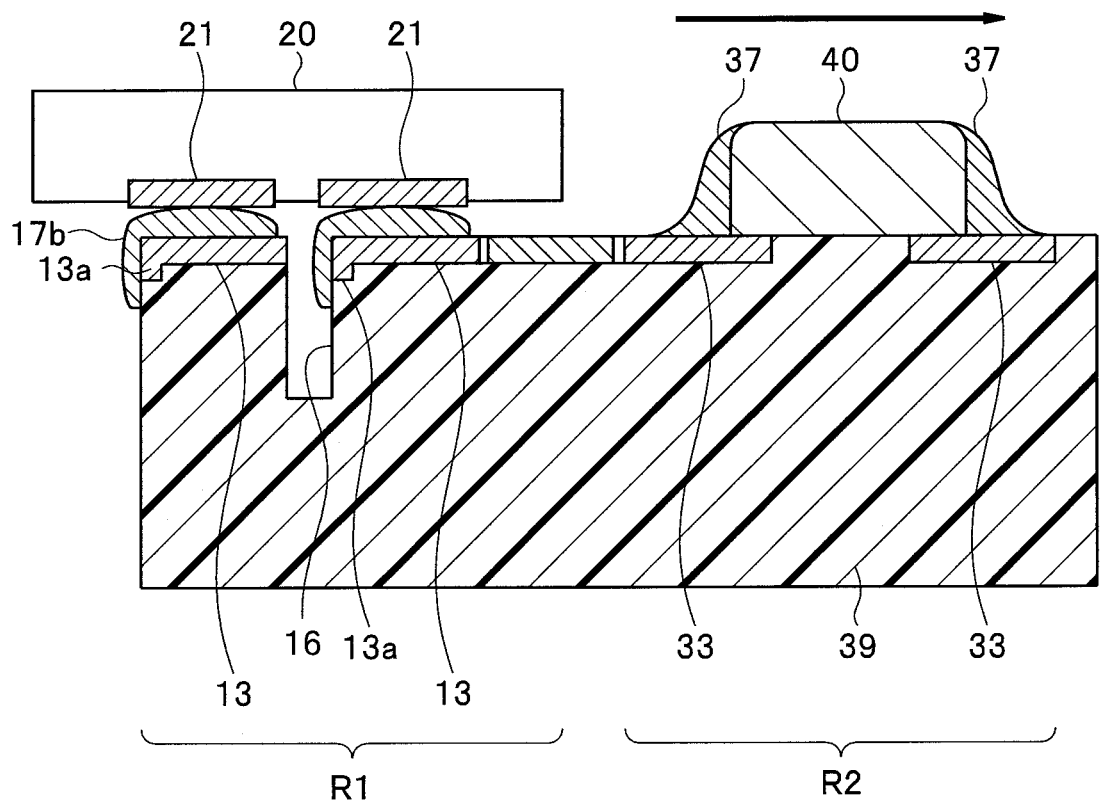
FIG. 8 is a cross-sectional view illustrating the same section as in FIG. 7 in the comparative example.
Figure 9:
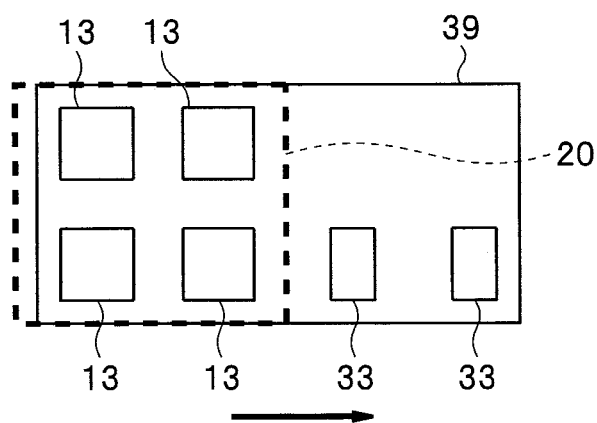
FIG. 9 is a plan view illustrating arrangement in FIG. 8.
Figure 10:
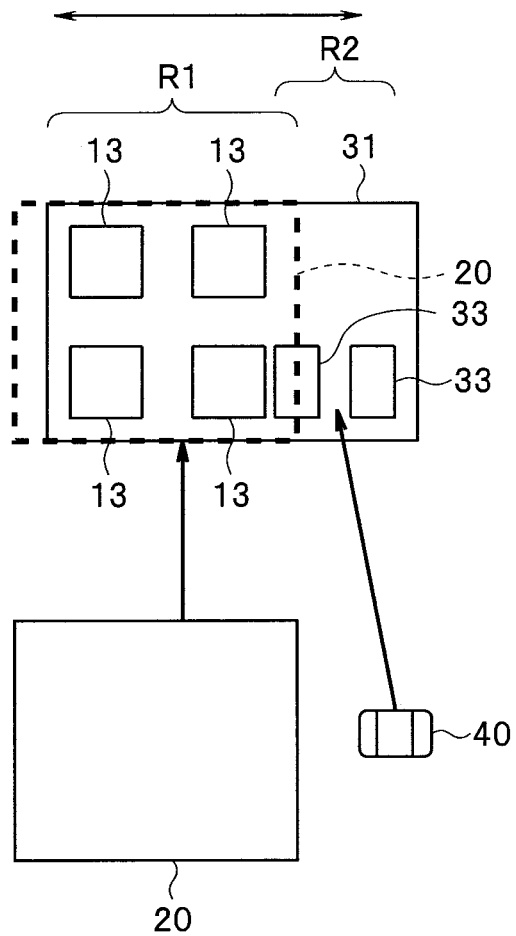
FIG. 10 is an explanatory diagram for description of effects of the present embodiment.
Figure 11:
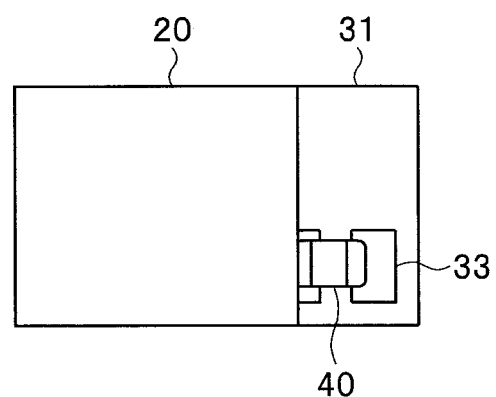
FIG. 11 is an explanatory diagram for description of effects of the present embodiment.

Subsequently, effects of the embodiment thus configured will be described below with reference to FIGS. 8 to 11. FIG. 8 is a cross-sectional view illustrating the same section as in FIG. 7 in the comparative example, and FIG. 9 is a plan view illustrating arrangement in FIG. 8. FIGS. 10 and 11 are explanatory diagrams for description of the effects of the present embodiment.

FIG. 8 illustrates, for comparison, a mount table 39 in which the heights of the first electrode mounting surface 14 and the second electrode mounting surface 34 in FIG. 7 are identical, in other words, that has a flat upper surface. In FIG. 8, the dimensions of regions R1 and R2 in the direction of an arrow parallel to the lands 13 are the same as those of the respective regions R1 and R2 in FIG. 7.

In the example illustrated in FIG. 8, the electronic component 20 and the chip component 40 are soldered to the lands 13 and 33 on the same plane. Thus, as illustrated in FIG. 9, the lands 13 and 33 are disposed at positions where the region R1 in which the electronic component 20 is disposed and the region R2 in which the chip component 40 is disposed can be positioned without overlapping in the direction of an arrow. In other words, the regions R1 and R2 need to be set without overlapping in the direction of the arrow.

FIG. 10 illustrates planar shapes of the electronic component 20 and the chip component 40 and a planar shape of the mount table 31 in FIG. 7. For example, an image pickup device is employed as the electronic component 20 and a chip capacitor is employed as the chip component 40. FIG. 11 illustrates the planar shapes after mounting.

When the electronic component 20 is mounted on the lands 13 by soldering, the electronic component 20 is disposed in the region R1 illustrated with a dashed line frame in FIG. 10. The chip component 40 is mounted on the land 33 by soldering. The region R1 in which the electronic component 20 is mounted and the region R2 in which the chip component 40 is mounted overlap each other in the direction of arrows. Since the first electrode mounting surface 14 and the second electrode mounting surface 34 have a height difference therebetween, the region R1 in which the electronic component 20 is disposed and the region R2 in which the chip component 40 is disposed can two-dimensionally overlap each other without problem.

As illustrated in FIG. 11, the chip component 40 and the electronic component 20 are disposed in two-dimensionally overlapping regions. As a result, the dimension of the electronic module in the direction of arrows can be reduced as compared to the example in FIGS. 8 and 9.

In this manner, in the present embodiment, since the first electrode mounting surface on which an electronic component is mounted and the second electrode mounting surface on which a chip component is mourned have a height difference therebetween, it is possible to dispose the electronic component and the chip component in two-dimensionally overlapping regions, thereby achieving device size reduction.

Third Embodiment

Figure 12:
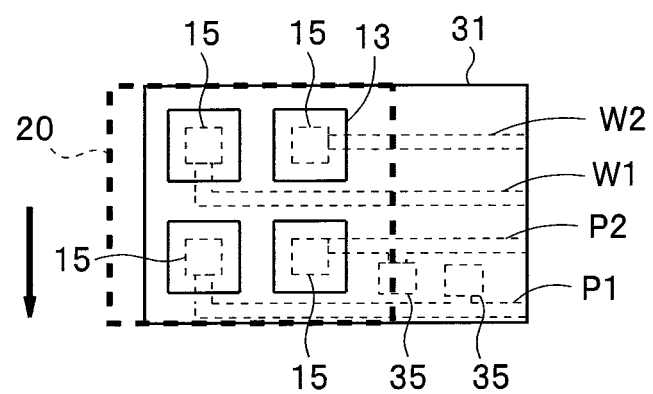
FIG. 12 is an explanatory diagram illustrating a third embodiment of the present invention.
Figure 13:
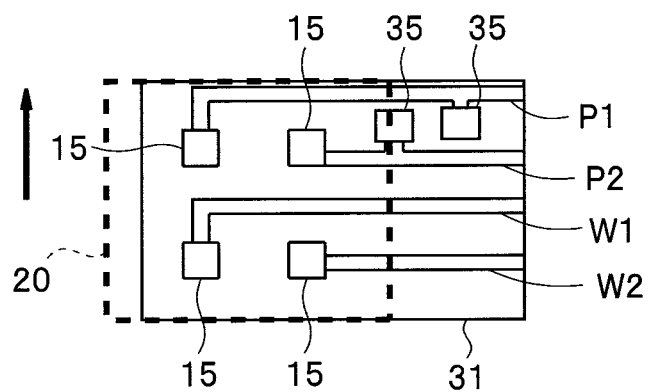
FIG. 13 is an explanatory diagram illustrating the third embodiment of the present invention.
Figure 14:
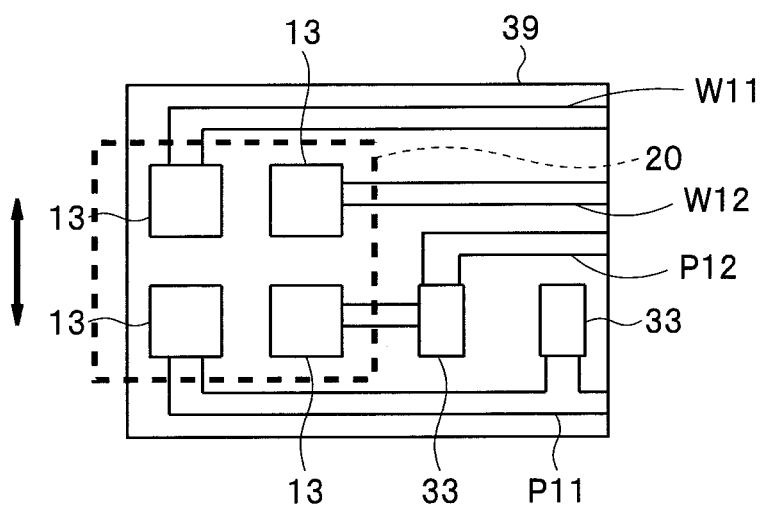
FIG. 14 is an explanatory diagram illustrating wiring arrangement of an electronic module in FIG. 8 as a comparative example.

FIGS. 12 and 13 are explanatory diagrams illustrating a third embodiment of the present invention. In FIGS. 12 and 13, the same constituent component as in FIG. 7 is denoted by the same reference sign, and description thereof will be omitted. FIG. 12 illustrates a planar shape of wiring arrangement of the electronic module in FIG. 7 when viewed from the upper surface side of the mount table, and FIG. 13 illustrates a planar shape of wiring arrangement of the electronic module in FIG. 7 when viewed from the bottom surface side of the mount table. FIG. 14 is an explanatory diagram illustrating, as a comparative example, wiring arrangement of the electronic module in FIG. 8. FIGS. 12 to 14 illustrate an example in which wires are aligned on one end side of the electronic module (the right side of the sheet) when externally extended. Note that the present embodiment is applicable to a wiring pattern of any extending direction.

In the present embodiment, a wiring pattern is formed on the hack surface of a mount table by using a via hole formed in the mount table. Accordingly, the front surface side of the mount table can have a configuration mainly based on consideration of a component mounting function, and the bottom surface side of the mount table can have a configuration mainly based on consideration of a wiring function.

FIG. 14 illustrates, for comparison with FIGS. 12 and 13, an example in which wiring patterns P11, P12, W11, and W12 are formed on an upper surface (on which the lands 13 and 33 are formed) of the mount table 39 in the electronic module in FIG. 8. The wiring patterns P11 and P12 are wiring patterns for power source lines and connected to a pair of respective lands 13 connected to a pair of respective electrodes 21 of the electronic component 20 for a power source. The wiring patterns P11 and P12 are also connected to a pair of respective lands 33 for mounting of the chip component 40.

The wiring patterns W11 and W12 are wiring patterns for signals and connected to a pair of respective lands 13 for signals to the electronic component 20.

The wiring pattern W12 is linearly formed from the corresponding land 13. However, the pair of lands 13 to which the wiring patterns W11 and W12 are connected are disposed side by side in the extending directions of the wiring patterns W11 and W12, and thus, to bypass a land 13, the wiring pattern W11 is routed from the corresponding land 13 in a marginal direction of the mount table 39, which is illustrated with an arrow in FIG. 14, and then bent at right angle and wired in parallel to the wiring pattern W12.

This is the same for the wiring patterns P11 and P12. In order to bypass a land 33, the wiring pattern P11 is routed from the corresponding land 33 in the marginal direction of the mount table 39, which is illustrated with an arrow in FIG. 14, and then bent at right angle and wired in parallel to the wiring pattern P12. Note that, to bypass a land 33, the wiring pattern P12 is routed from the corresponding land 33 in a center direction of the mount table 39, which is illustrated with an arrow in FIG. 14, and then bent at right angle and wired in parallel to the wiring pattern P11.

Thus, in the comparative example in FIG. 14, spaces for wiring of the wiring patterns P11 and W11 need to be provided in the marginal direction of the mount table 39, which is illustrated with an arrow. For example, in the example illustrated in FIG. 14, the size of the mount table 39 in the direction of arrows needs to be sufficiently larger than the size of the electronic component 20.

In this manner, in the comparative example, since mounting and wiring are performed on the front surface of the mount table 39, a wiring pattern needs to be formed with a bypass of lands, which leads to increase of the area of the electronic module.

However, in the present embodiment, wiring patterns for driving the electronic component 20 and the chip component 40 are formed on the back side (bottom surface) of the mount table 31. For example, in FIG. 7, the wiring pattern 36 connecting a via hole 15 and the corresponding via hole 35 is formed on the bottom surface of the mount table 31.

In the example illustrated in FIGS. 12 and 13, wiring patterns P1, P2, W1, and W2 are formed on the bottom surface of the mount table 31. The wiring patterns P1 and P2 are wiring patterns for power source lines and connected to a pair of respective via holes 15 for the power source of the electronic component 20. The wiring patterns P1 and P2 are also connected to a pair of respective via holes 35 for mounting of the chip component 40.

The wiring patterns W1 and W2 are wiring patterns for signals and connected to a pair of respective via holes 15 for signals to the electronic component 20.

The lands 13 and 33 need to be formed with sufficiently large area in accordance with a solder ball diameter (not illustrated) at mounting, the size of the chip component 40, and the like based on consideration of the position accuracy of component mounting, the position accuracy of solder application, the strength of component mounting, and the like. Thus, the area of occupation by the lands 13 and 33 on the upper surface of the mount table 31 is relatively large. Furthermore, reduction of the size of a wiring pattern is limited due to constraint of lasering, plating processes and the like, and thus formation of such a wiring pattern on the upper surface of the mount table 31 leads to device size increase.

The cross-sectional areas of the via holes 15 and 35 on the bottom surface side of the mount table 31 are larger than the cross-sectional areas thereof on the upper surface side, but the sizes of regions occupied by the via holes 15 and 35 on the bottom surface of the mount table 31 are sufficiently small as compared to the areas of the lands 13 and 33. For this reason, in the present embodiment, wiring patterns are formed on the back surface side of the mount table 31 on which the lands 13 and 33 are not formed. Accordingly, it is expected that the freedom of arrangement of the wiring patterns P1, P2, W1, and W2 on the bottom surface side of the mount table 31 increases.

In the example illustrated in FIGS. 12 and 13, the wiring pattern P2 can be linearly formed from the corresponding via hole 15 to a marginal part, depending on the relation between the position of the via hole 15 and the position of the via hole 35. The pair of via holes 15 to which the wiring patterns P1 and P2 are connected are disposed side by side in the extending directions of the wiring patterns P1 and P2. Thus, in the example illustrated in FIGS. 12 and 13 as well, the wiring pattern P1 is routed in a marginal direction of the mount table 31, which is illustrated with an arrow in each of FIGS. 12 and 13, and then bent at right angle and wired in parallel to the wiring pattern P2. In this case as well, the distance of bypassing in the marginal direction of the mount table 31 is shorter than in the example illustrated in FIG. 14 by decrease of the planar size of the via hole 15. As a result, in the example illustrated in FIGS. 12 and 13, the size of the mount table 31 in the direction of arrows does not need to be larger than the size of the electronic component 20.

Moreover, the pair of via holes 15 to which the wiring patterns W1 and W2 are connected are disposed side by side in the extending directions of the wiring patterns W1 and W2, and thus the wiring pattern W1 needs to bypass a via hole 15. However, in this case as well, since the size of the via hole 15 on the bottom surface of the mount table 31 is sufficiently small, the wiring pattern W1 is routed toward the via hole 15 side in the direction illustrated with an arrow in each of FIGS. 12 and 13, and then bent at right angle and wired in parallel to the wiring pattern W2 between via holes 15. Thus, in this case, the size of the mount table 31 in the direction of arrows does not need to be increased for the wiring pattern W1.

In this manner, in the present embodiment, a wiring pattern is formed on the bottom surface side of the mount table on which the area of occupation by each via hole is relatively small. Specifically, the front surface side of the mount table is mainly used for component mounting, and the back surface side of the mount table is used for wiring. Accordingly, consideration of lands is not needed at formation of a wiring pattern, which improves the freedom of arrangement of the wiring pattern. Moreover, mounting with high space efficiency is possible on the front side of the mount table. As a result, device size reduction can be achieved.

Note that, in the above-described example, the present embodiment is applied to the example illustrated in FIG. 7, but is applicable to the first embodiment in FIG. 1.

Fourth Embodiment

Figure 15:
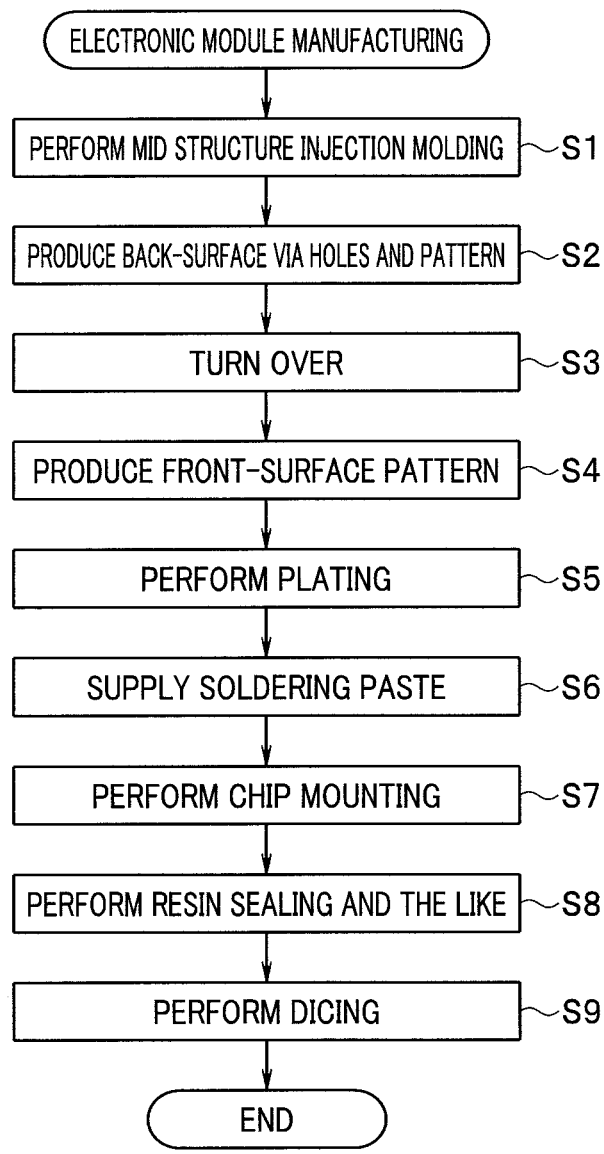
FIG. 15 is a flowchart illustrating a fourth embodiment of the present invention.
Figure 16:
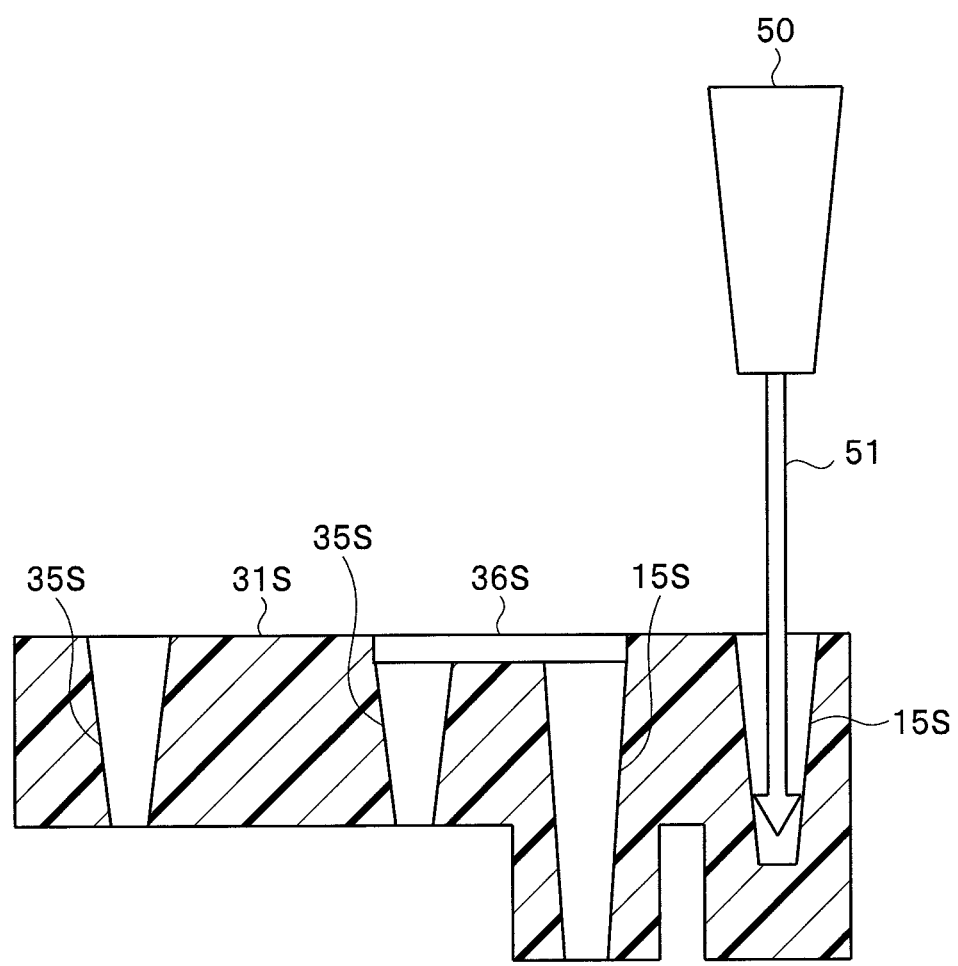
FIG. 16 is an explanatory diagram for description of application of processes in FIG. 15 to an electronic module in FIG. 7.
Figure 17:
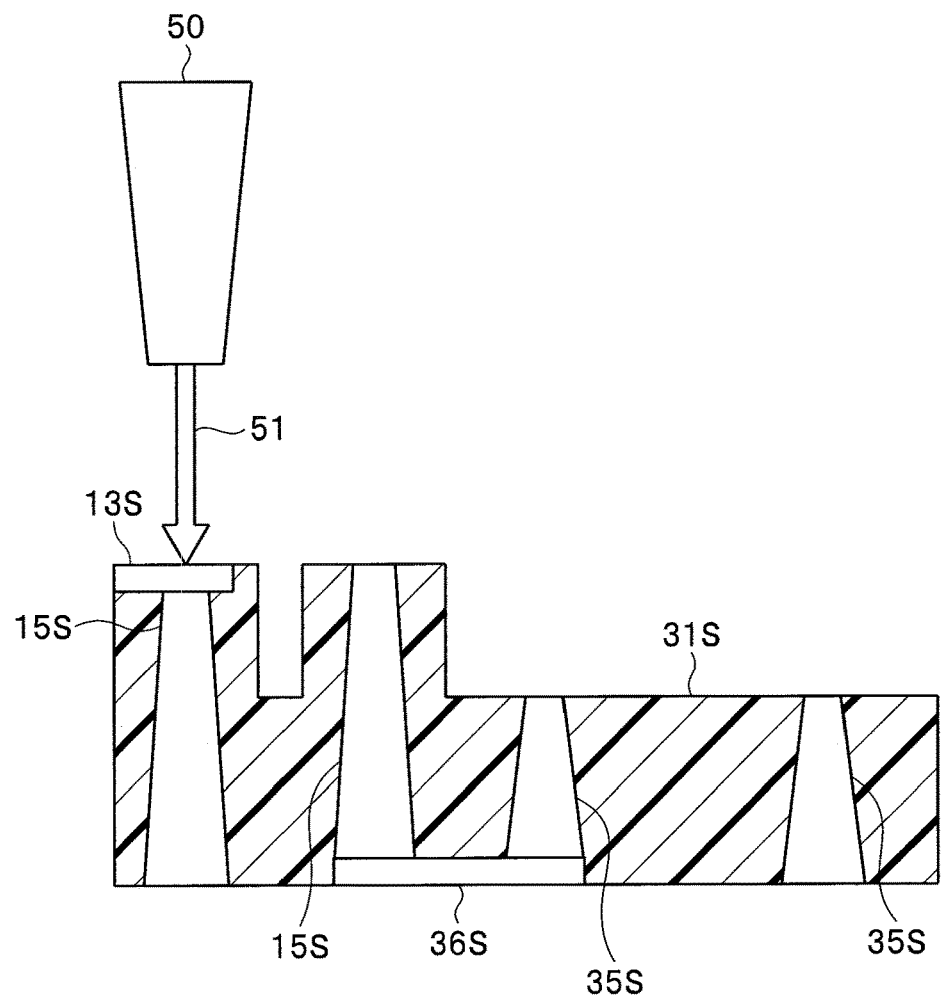
FIG. 17 is an explanatory diagram for description of application of the processes in FIG. 15 to the electronic module in FIG. 7.
Figure 18:
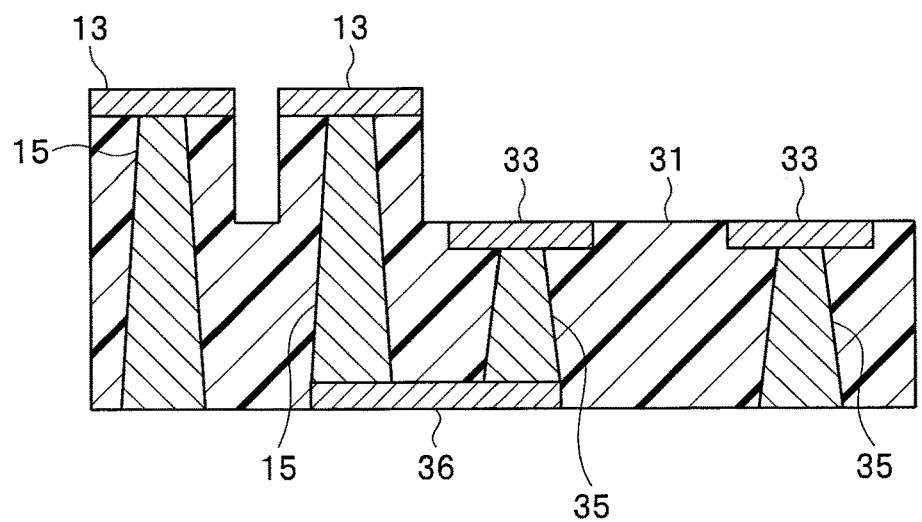
FIG. 18 is an explanatory diagram for description of application of the processes in FIG. 15 to the electronic module in FIG. 7.

FIG. 15 is a flowchart illustrating a fourth embodiment of the present invention. FIG. 15 illustrates a method of manufacturing the electronic module in each above-described embodiment in the order of processes. FIGS. 16 to 18 are explanatory diagrams for description of application of the processes in FIG. 15 to the electronic module in FIG. 7. Note that the present embodiment provides an example in which the electronic module is manufactured by the MID technology.

When the electronic module is manufactured by the MID technology, a predetermined resin material is set to a mold and injection molding is performed at step S1. Multiple pieces may be manufactured with a plurality of molds set to a runner. Subsequently at step S2, via holes and wiring patterns are produced on the back surface.

A molded product 31S to be the mount table 31 is produced through step S1. FIG. 16 illustrates pattern formation on the molded product 31S. A laser device 50 emits a laser beam 51 illustrated with an arrow from the back surface side of the molded product 31S corresponding to the back surface of the mount table 31 and forms openings 15S and 35S corresponding to the via holes 15 and 35. Note that FIG. 16 illustrates a state halfway through formation of the last opening 15S. In addition, a pattern 36S to be the wiring pattern 36 is formed through scanning along the front surface of the molded product 31S with the laser beam 51 from the laser device 50.

Note that sectional sizes of the openings 15S and 35S formed by laser-beam irradiation for via-hole formation are set to be appropriate sizes with which openings are formed on the front surface side of the molded product 31S but openings are not formed on the back surface side at soldering to be described later.

When $\phi 1$ represents the diameters of the via holes 15 and 35 on the lands 13 and 35 side, $\phi 2$ represents the diameters of the via holes 15 and 35 on the back surface side, T represents the distance (the thickness of the mount table 31) from the bottom surface of the mount table 31 to each of the first electrode mounting surface 14 and the second electrode mounting surface 34, and Pt represents the thickness of plating, manufacturing is preferably performed so that Expression (1) described below is satisfied.

$$\phi 1 = T/10 + Pt, \phi 2 = T/5 + Pt \quad (1)$$

When lasering is provided so that Expression (1) above is satisfied, the via holes 15 and 35 can be blocked on the upper surface side of the mount table 31 at plating processing, and thus prevention of solder flow and filling of the via holes with a sealing member can be omitted.

Subsequently at step S3, the molded product 31S is turned over, and patterns to be the lands 13 and 15 are formed by irradiating the front surface side of the molded product 31S with the laser beam 51 from the laser device 50 at step S4. Note that FIG. 17 illustrates a state halfway through formation of a pattern 13S corresponding to a land 13.

Next at step S5, plating processing is provided. The patterns 36S, 13S and the like are activated and roughed through irradiation with the laser beam 51, and only pattern formation parts of the patterns 36S, 13S and the like are metallized. Plating enters the openings 15S and 35S and forms films therein. As a result, the mount table 31 including the via holes 15 and 35, the lands 13 and 33, and the wiring pattern 36 is formed as illustrated in FIG. 18.

Subsequently, soldering paste for mounting the electronic component 20 on the lands 13 and 33, the chip component 40 is supplied (step S6). Next at step S7, the electronic component 20 and the chip component 40 are mounted on the lands 13 and 33, respectively.

Subsequently, a predetermined space surrounding the electronic module after the mounting is filled with predetermined resin and sealed (step S8). Lastly, in a case in which multiple pieces are manufactured, a cutting process (dicing) is executed (step S9) to complete the electronic module. Note that the cutting process does not necessarily need to be the last process but may be, for example, right after the molding process.

In this manner, in the present embodiment, the electronic module can be manufactured by the MID technology.
(Modification)

Figure 19:
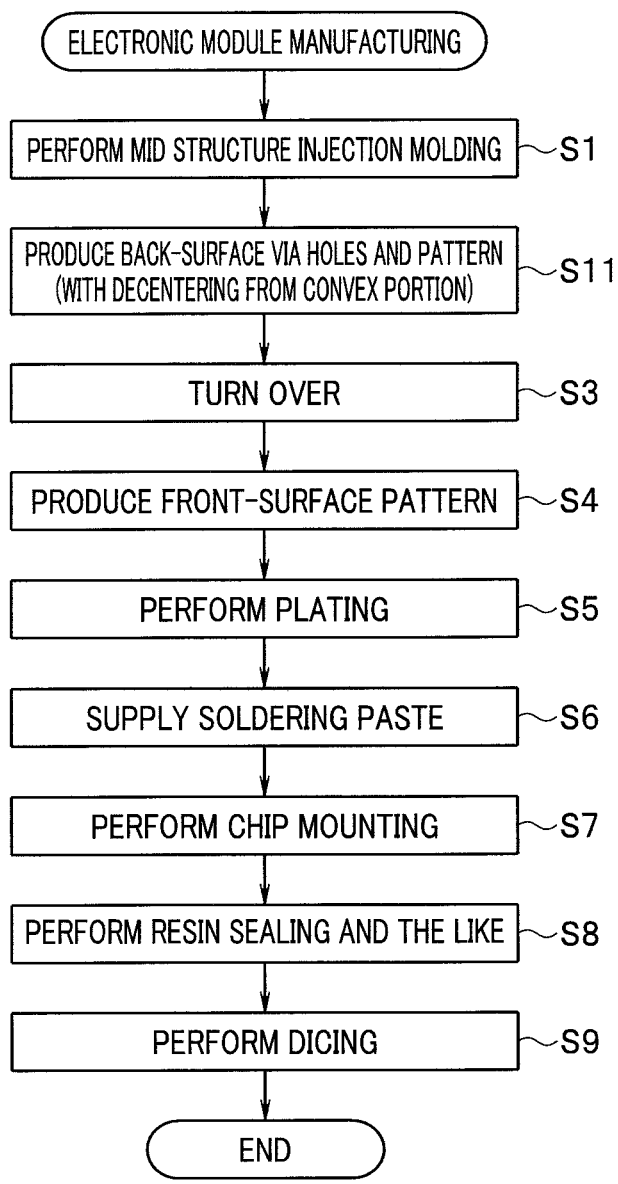
FIG. 19 is a flowchart illustrating a modification of a manufacturing method.

FIG. 19 is a flowchart illustrating a modification of the manufacturing method. In FIG. 19, the same procedure as in FIG. 15 is denoted by the same reference sign, and description thereof will be omitted.

The flowchart in FIG. 19 is different from the flowchart, in FIG. 15 in that step S11 is employed in place of step S2. At step S11, openings to be the via holes 15 and 35 are formed such that the centers of the openings are decentered from the centers of the lands 13 and 33 (centers of patterns concave portions) for forming the lands 13 and 33). In this case, the direction of the decentering may be set based on consideration of the extending directions of wiring patterns.

Figure 20:
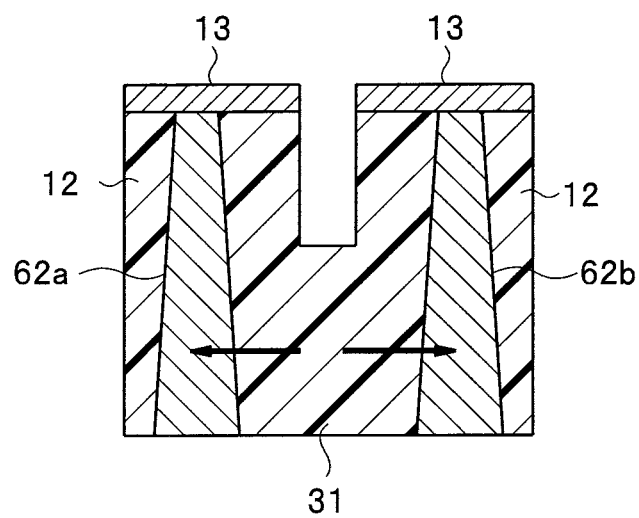
FIG. 20 is a cross-sectional view illustrating an example of an electronic module formed by employing the flowchart in FIG. 19.
Figure 21:
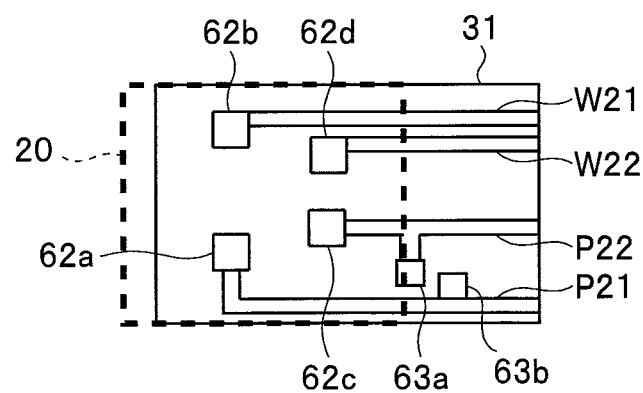
FIG. 21 is a plan view illustrating the electronic module in FIG. 20 when viewed from top.

FIG. 20 is a cross-sectional view illustrating an example of an electronic module formed by employing the flowchart in FIG. 19. FIG. 21 is a plan view illustrating the electronic module in FIG. 20 when viewed from the bottom surface side. In FIGS. 20 and 21, the same constituent component as in FIGS. 7, 12, and 13 is denoted by the same reference sign, and description thereof will be omitted.

The electronic module illustrated in FIG. 20 is different from the electronic module in FIG. 7 in that via holes 62a to 62d are employed in place of four via holes 15. The via holes 62a and 62b are formed at positions decentered from the centers of the respective lands 13 in directions separating from each other as illustrated with arrows in FIG. 20. Accordingly, the via holes 62a and 62b at the bottom surface of the mount table 31 are positioned on respective margin vicinity sides of the mount table 31.

Although not illustrated in FIG. 20, the via holes 62c and 62d are formed at positions decentered from the centers of the respective lands 13 in directions opposite to the arrows in FIG. 20, in other words, directions approaching each other. Accordingly, the via holes 62c and 62d at the bottom surface of the mount table 31 are positioned on the center side of the mount table 31. In addition, via holes connected to the lands 33 in FIG. 7 may be formed at positions decentered from the centers of the lands 33.

FIG. 21 illustrates the state of the back surface of the mount table 31 in this case. In the example illustrated in FIG. 21, the wiring patterns P21, P22, W21, and W22 are formed on the bottom surface of the mount table 31. The wiring patterns P21 and P22 are wiring patterns for power source lines and connected to a pair of respective via holes 62a and 62c for the power source of the electronic component 20. The wiring patterns P21 and P22 are also connected to a pair of respective via holes 63a and 63b for mounting of the chip component 40. The wiring patterns W21 and W22 are wiring patterns for signals and connected to a pair of respective via holes 62b and 62d for signals to the electronic component 20.

As described above, the via holes 62a and 62b are decentered to the margin sides of the mount table 31, and the via holes 62c and 62d are decentered on the center side of the mount table 31. Specifically, in the extending directions of the wiring patterns P21, P22, W21, and W22, the disposition positions of the via holes 62a and 62c do not overlap or the overlapping is small and the disposition positions of the via holes 62b and 62d do not overlap or the overlapping is small. As a result, not only the wiring pattern W22 is linearly formed but also the wiring pattern W21 can be linearly formed because the wiring pattern W21 does not need to bypass the via hole 62d. In this manner, the freedom of arrangement of the wiring patterns P21, P22, W21, and W22 can be further improved.

Note that, in the example illustrated in FIG. 21, to bypass the via holes 63a and 63b, the wiring pattern P21 is routed in the marginal part direction of the mount table 31 and then bent at right angle and wired in parallel to the wiring pattern P22, but the amount of the bypassing is relatively small. Moreover, the wiring pattern P21 can be linearly wired without bypassing, depending on the dimensions of the mount table 31 and the sizes of the via holes 63a and 63b.

In this manner, the modification has a configuration in which each via hole is formed with decentering from the center of a land, to thereby provide an advantage that the freedom of arrangement of a wiring pattern can be further improved when the wiring pattern is formed on the back surface of the mount table.
(Modification)

Figure 22:
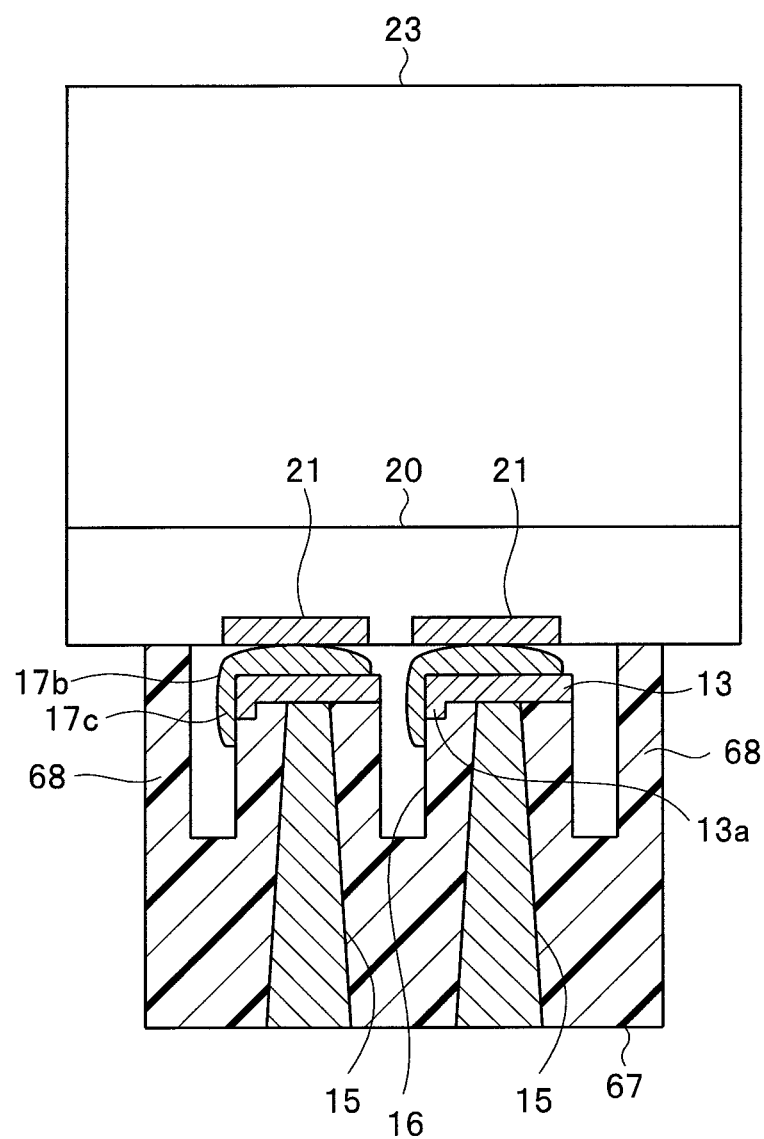
FIG. 22 is a cross-sectional view illustrating a modification of an electronic module.

FIG. 22 is a cross-sectional view illustrating a modification of the electronic module. In FIG. 22, the same constituent component as in FIG. 7 is denoted by the same reference sign, and description thereof will be omitted.

The example illustrated in FIG. 22 is an application to an image pickup module in which an optical system 23 is attached to an image pickup device employed as the electronic component 20. The size of the optical system 23 in a vertical direction is larger than a horizontal size of the electronic component 20. Thus, it is thought that when the electrodes 21 are soldered to the lands 13 by the solder 17b, the optical axis of the optical system 23 tilts and it is difficult to accurately point the optical axis to a defined direction in some cases. For this reason, the present modification includes a support member 68 that supports the electronic component 20 to which the optical system 23 is attached.

A mount table 67 is different from the mount table 31 in that the mount table 67 includes the support member 68. The support member 68 is formed, for example, in a column shape at an end part of the mount table 67 and provided to support the electronic component 20 on which the optical system 23 is mounted. Specifically, the support member 68 has a height from a bottom surface of the mount table 67 to an upper surface of the solder 17b, and an upper surface of the support member 68 contacts the bottom surface of the electronic component 20 after mounting.

In the example illustrated in FIG. 22, the support member 68 is provided at each end of the mount table 67, but may be provided only at one end part of the mount table 67 or may be provided at one or more places of the mount table 67 at which the mounted electronic component 20 can be supported.

With the support member 68, it is possible to reliably support the electronic component 20, thereby preventing tilt of an image pickup direction from a direction perpendicular to the lands 13.

Fifth Embodiment

Figure 23:
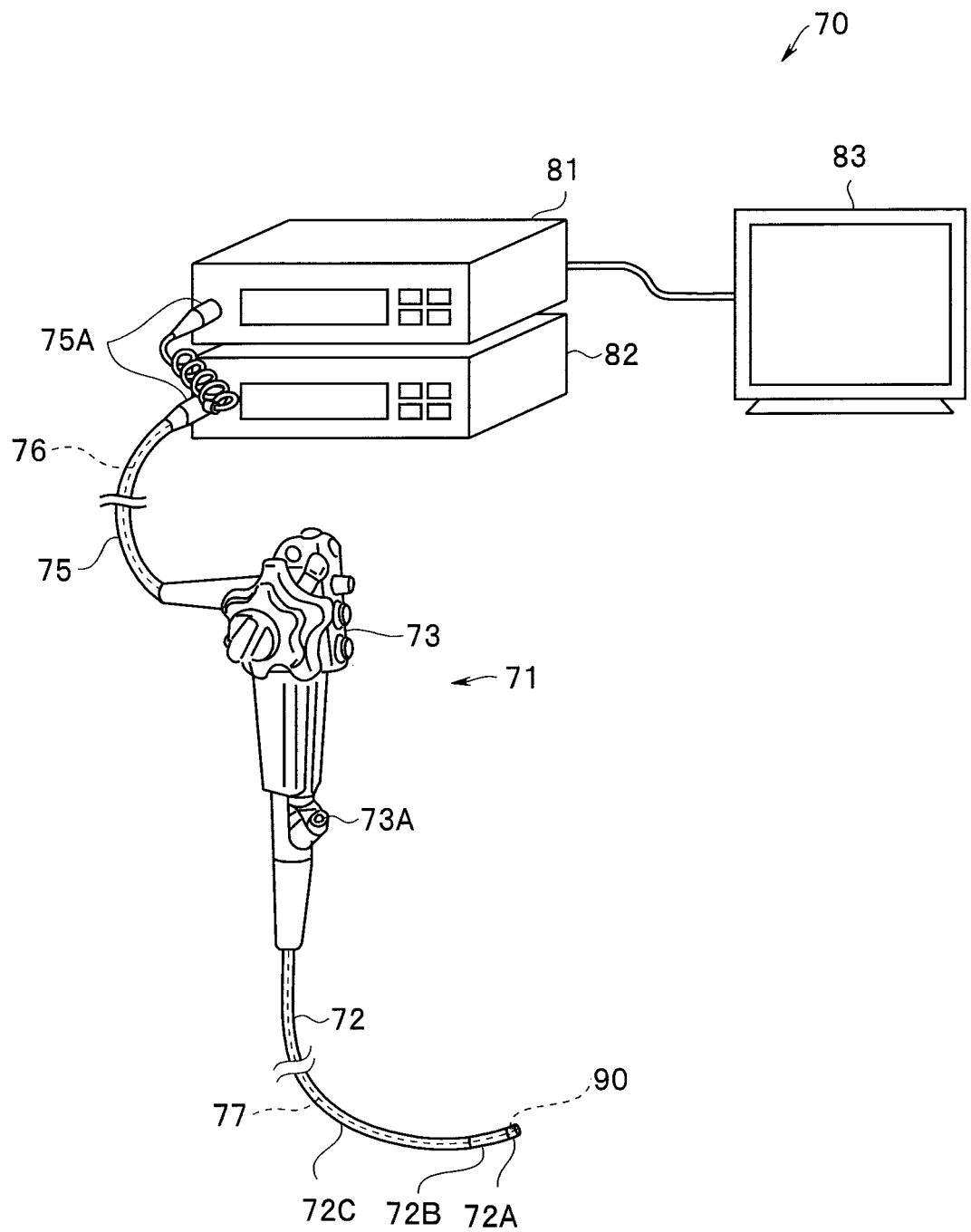
FIG. 23 is a diagram illustrating a fifth embodiment.

FIG. 23 is a diagram illustrating a fifth embodiment. The present embodiment is an application of each above-described electronic module to an endoscope system.

As illustrated in FIG. 23, an endoscope system 70 includes an endoscope 71, a video processor 81, a light source device 82, and a monitor 83. The endoscope 71 includes an insertion portion 72 that can be inserted into the body cavity of a subject. A distal end portion 72A of the insertion portion 72 includes an image pickup unit 90 (not illustrated in FIG. 23) for picking up an image of a body cavity image of the subject. The image pickup unit 90 performs image pickup inside the subject and outputs an image pickup signal.

An operation portion 73 provided with various buttons and the like for operating the endoscope 71 is disposed on a proximal end side of the insertion portion 72 of the endoscope 71. The operation portion 73 includes a treatment instrument insertion port 73A of a channel through which a treatment instrument such as a biological forceps, an electrocautery scalpel, or an examination probe is inserted into the body cavity of the subject. Note that a channel opening is provided at a distal end of the insertion portion 72.

The insertion portion 72 is constituted by the distal end portion 72A at which the image pickup unit 90 is disposed, a bending portion 72B that is freely bendable and continuously provided on the proximal end side of the distal end portion 72A, and a flexible tube portion 72C continuously provided on the proximal end side of the bending portion 72B. The bending portion 72B bends in accordance with an operation of the operation portion 73.

A signal cable 76 connected to the image pickup unit 90 provided at the distal end portion 72A is inserted in a universal code 75 disposed on the proximal end portion side of the operation portion 73. The universal code 75 is connected to the video processor 81 and the light source device 82 through a connector 75A. The video processor 81 controls the entire endoscope system 70 and also performs signal processing on an image pickup signal output from the image pickup unit 90 and outputs an image signal. The monitor 83 is provided with the image signal from the video processor 81 and displays an endoscope image.

The light source device 82 includes, for example, a white LED and emits white light. The white light emitted from the light source device 82 is guided to an illumination optical system (not illustrated) of the distal end portion 72A through a light guide (not illustrated) in which the universal code 75 is inserted, and an object is irradiated with the white light.

In the present embodiment, the electronic module in each above-described embodiment may be employed as the image pickup unit 90.

Figure 24:
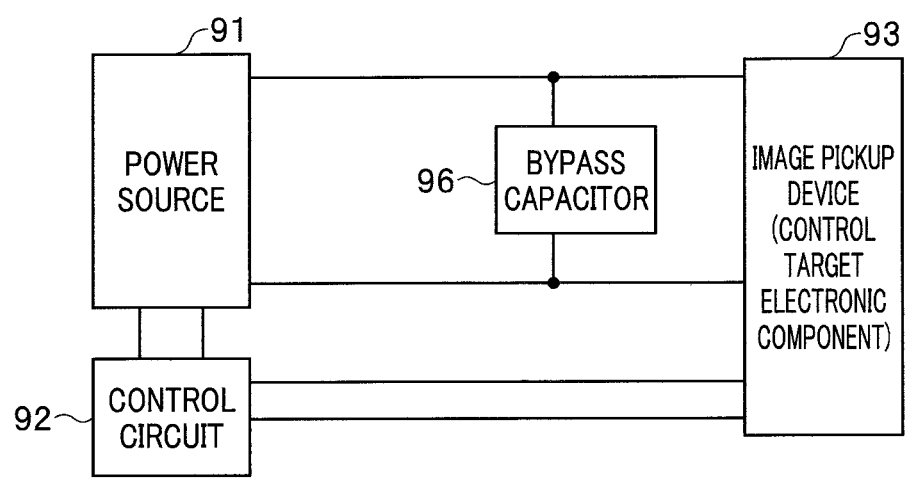
FIG. 24 is a circuit diagram illustrating the configuration of a circuit configured to drive an image pickup unit 90.

FIG. 24 is a circuit diagram illustrating the configuration of a circuit configured to drive the image pickup unit 90. The image pickup unit 90 includes an image pickup device 93 as a control target electronic component (IC) in FIG. 24 and a bypass capacitor 96, and the image pickup device 93 and the bypass capacitor 96 correspond to the electronic component 20 and the chip component 40, respectively, in each above-described embodiment. A power source 91 and a control circuit 92 in FIG. 24 are included in the video processor 81. The video processor 81 and the image pickup unit 90 provided at the distal end portion 72A are connected to each other through two signal lines and two power source lines inserted in the insertion portion 72.

Power voltage generated by the power source 91 is supplied to two terminals of the image pickup device 93 through two power source lines. The bypass capacitor 96 (equivalent to the chip component 40) for removing noise is connected between the two terminals.

The control circuit 92 and the image pickup device 93 are connected to each other through the two signal lines. The control circuit 92 operates with supply of the power voltage from the power source 91 and drives the image pickup device 93 by performing signal communication with the image pickup device 93 (equivalent to the electronic component 20) through the two signal lines.

FIGS. 25 to 28 are diagrams for description of an example of the image pickup unit 90 including the electronic module according to each above-described embodiment. In the illustrated example, an image pickup unit corresponding to a front-viewing endoscope is employed as the image pickup unit 90. In FIGS. 25 to 28, the same constituent component as in FIGS. 7 and 22 to 24 is denoted by the same reference sign and description thereof will be omitted. Note that the image pickup unit 90 is constituted by the electronic module in each above-described embodiment and an image pickup module 95. For example, when the image pickup unit 90 is manufactured by using the MID technology, wiring patterns can be easily formed on a mount table having a complicate three-dimensional shape.

Figure 25:
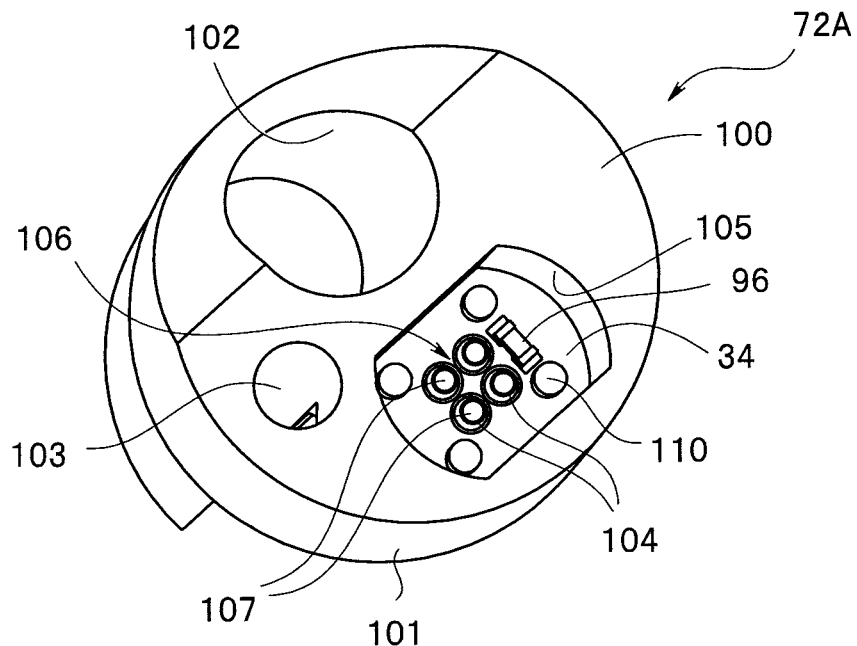
FIG. 25 is a perspective view of a mounting module 100 included in a distal end portion 72A.
Figure 26:
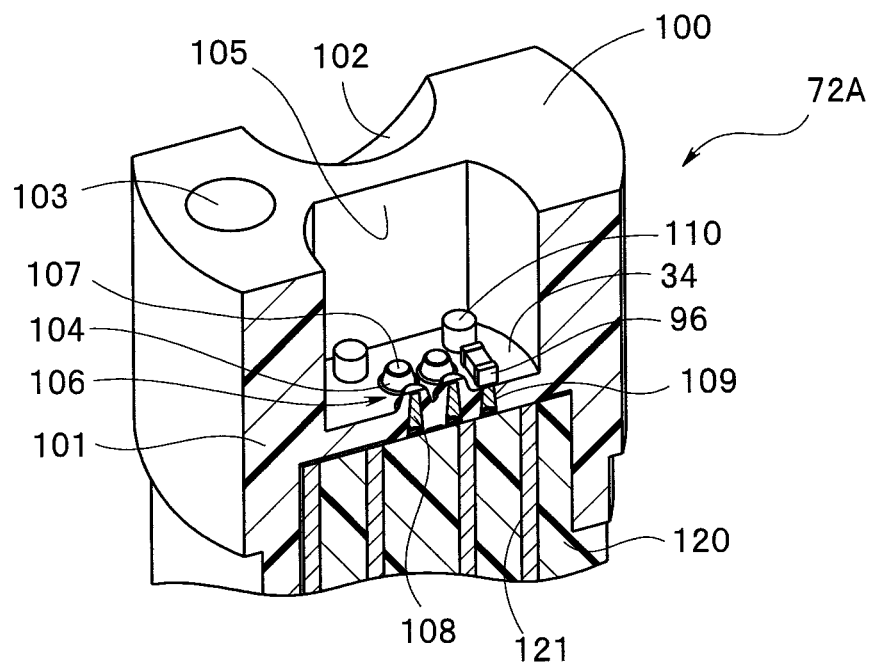
FIG. 26 is a breakaway perspective view illustrating a sectional shape of part of the distal end portion 72A.
Figure 27:
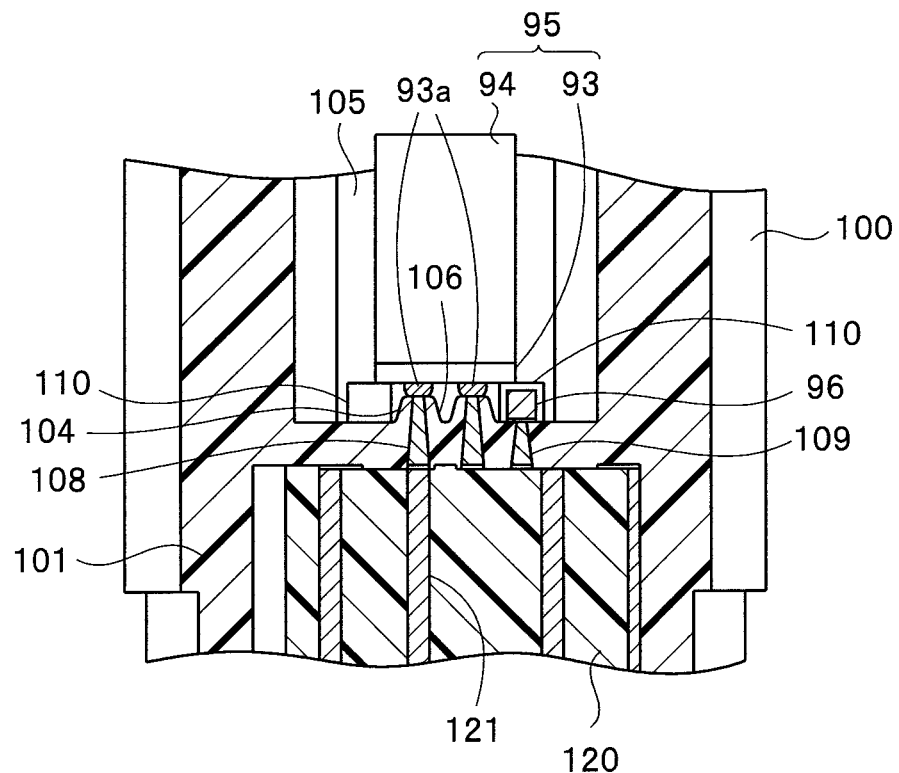
FIG. 27 is a diagram for description of an example of the image pickup unit 90 including an electronic module according to each embodiment.
Figure 28:
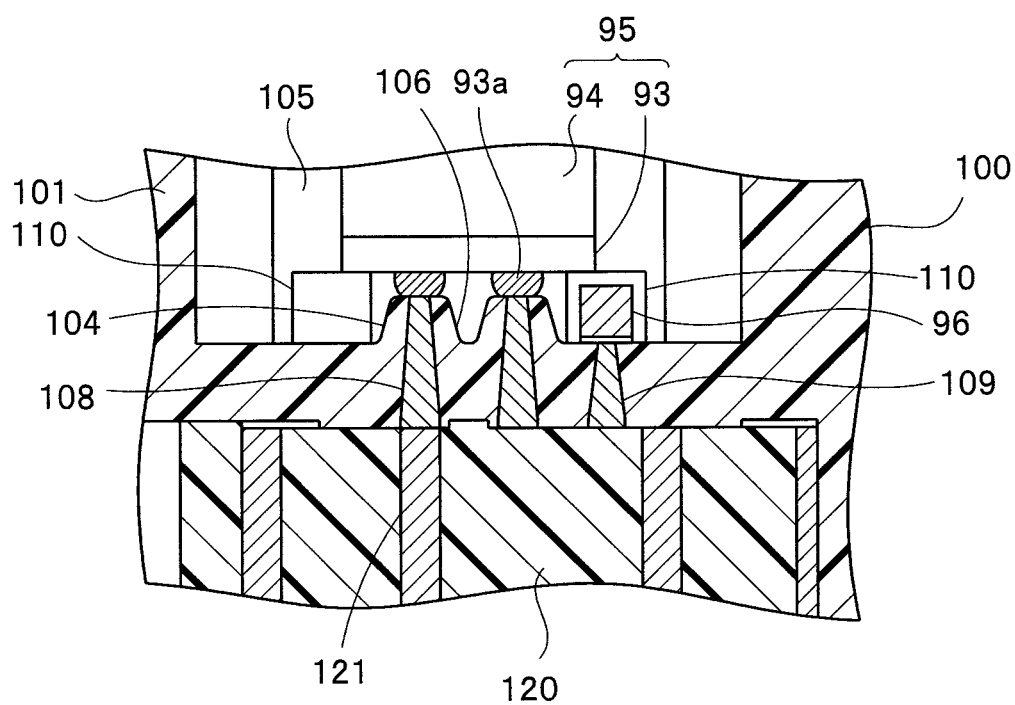
FIG. 28 is a diagram for description of an example of the image pickup unit 90 including an electronic module according to each embodiment.

The distal end portion 72A is constituted by two modules of a mounting module 100 and a wiring module 120. FIGS. 25 to 28 illustrate the distal end portion 72A. FIG. 25 is a perspective view of the mounting module 100 constituting the distal end portion 72A. FIG. 26 is a breakaway perspective view illustrating a sectional shape of part of the distal end portion 72A. FIGS. 27 and 28 are cross-sectional views of the distal end portion 72A.

The mounting module 100 corresponds to the electronic module in each above-described embodiment. The mounting module 100 is attached on the distal end side of the wiring module 120 and provided at the distal end of the insertion portion 72 with the proximal end side of the wiring module 120 being provided continuously with the bending portion 72B. In the mounting module 100, a part at which a channel opening 102 for inserting and removing a distal end of a treatment instrument inserted through the treatment instrument insertion port 73A is formed and a part at which an illumination optical system 103 is formed are provided outside a part at which the image pickup module 95 is housed.

A treatment instrument inserted in a treatment instrument insertion channel may extend to outside through the channel opening 102. Note that a small-sized endoscope can protrude out of the channel opening 102 through the treatment instrument insertion channel. The non-illustrated light guide inserted in the universal code 75 and the insertion portion 72 from the light source device 82 is guided to the illumination optical system 103, and illumination light is emitted to an object from the illumination optical system 103.

The mounting module 100 includes a mount table 101. The mount table 101 is a housing provided with a cavity (recess) part 105 and serves as a distal end rigid portion of the endoscope. The cavity part 105 is a concave portion having a substantially rectangular parallelepiped shape with a pair of curved wall surfaces facing each other, and has a size with which the image pickup module 95 can be substantially housed. The image pickup module 95 is mounted on the cavity part 105.

The mount table 101 has the same configuration as the mount table 31 in FIG. 7. Specifically, the mount table 101 includes a plurality (four in FIGS. 25 and 26) of electrode mount parts 104, and a step part 106 is provided among the electrode mount parts 104. In the example illustrated in FIGS. 25 to 28, the four electrode mount parts 104 each having a substantially circular truncated cone shape protrude from the second electrode mounting surface 34 that is a bottom surface of the cavity part 105, thereby forming the step part 106 among the electrode mount parts 104.

A land 107 is formed on an upper surface of each electrode mount part 104, and a via hole 108 penetrating through the mount table 101 is formed from the land 107 to a bottom surface of the mount table 101. Note that an upper surface of the mount table 101 at the electrode mount part 104 (≈upper surface of the land 107) is the first electrode mounting surface. Non-illustrated solder is pasted on each land 107 to solder the four electrodes of the image pickup device, and accordingly, the image pickup module 95 is mounted.

A pair of non-illustrated land formation regions are formed on the second electrode mounting surface 34, and via holes 109 penetrating from the second electrode mounting surface 34 of the mount table 101 to the bottom surface thereof are formed in the land formation regions. Then, non-illustrated lands are formed in the land formation regions, and the bypass capacitor 96 as a chip component is soldered to the lands.

Support members 110 protruding from the second electrode mounting surface 34 and supporting the image pickup module 95 are formed at four places around the four electrode mount parts 104 in the mount table 101.

FIGS. 27 and 28 illustrate a state in which the image pickup module 95 is mounted on the cavity part 105 of the mount table 101. Note that FIG. 28 illustrates part of FIG. 27 in an enlarged manner. The image pickup module 95 has a configuration in which an optical system 94 is mounted and integrated on the image pickup device 93 as an electronic component. Four electrodes 93a to which the two signal lines and the two power source lines are connected are provided on a bottom surface of the image pickup device 93. Solder is applied on the lands 107, and the electrodes 93a are pressed to the solder and soldered. At soldering, the bottom surface of the image pickup device 93 contacts and is supported by upper surfaces of the support members 110, and the image pickup module 95 is reliably mounted.

A concave portion is formed at the center of the bottom surface of the mount table 101, and the wiring module 120 is formed in a shape in which the wiring module 120 is fitted to the concave portion. Wiring patterns 121 connected to four wires inserted into the insertion portion 72 from the video processor 81, which are illustrated in FIG. 24, are formed in the wiring module 120.

Non-illustrated wiring patterns are formed on the bottom surface of the mount table 101. The wiring patterns on the bottom surface of the mount table 101 are connected to the four wiring patterns 121 penetrating inside the wiring module 120 when the wiring module 120 is fitted such that an upper surface thereof contacts an upper surface of the concave portion of the mount table 101. The via holes 108 and 109 are connected to the wiring patterns on the bottom surface of the mount table 101, and the four wires inserted into the insertion portion 72 from the video processor 81 are connected to the four electrodes 93a of the image pickup device 93 and the bypass capacitor 96 through the wiring patterns 121 in the wiring module 120, the wiring patterns on the bottom surface of the mount table 101, and the via holes 108 and 109.

Note that wiring patterns may be formed on the upper surface of the wiring module 120 instead of forming wiring patterns on the bottom surface of the mount table 101.

In this manner, in the present embodiment, the electronic module in each above-described embodiment is employed as the image pickup unit, and thus it is possible to shorten the distance between electrode mount parts while preventing short-circuit and reduce the size of the image pickup module, thereby achieving diameter reduction of the distal end portion.

In the example described above in the present embodiment, the electronic module in each above-described embodiment is applied to an endoscope, but is not limited thereto and is applicable to various electronic devices. For example, when a small-sized image pickup unit is configured as the electronic module in each above-described embodiment, it is possible to reduce the size of a space occupied by the image pickup unit as well as reduce the weight of the image pickup unit. Thus, when the image pickup unit is mounted on a movable object such as a wearable device, a vehicle, or a drone, it is possible to reduce a load at movement. Moreover, when the image pickup unit is applied to an endoscope distal end portion, it is possible to provide an endoscope that can be easily inserted.

The present invention is not limited to the above-described embodiments but may be, for example, changed or modified in various kinds of manners without departing from the gist of the present invention. For example, the present invention is applicable to a case in which a part described as an endoscope is replaced with a commercially available camera, an industrial camera, an on-board camera, a monitoring camera, or the like. Specifically, with the size-reduction feature of the present application, it is possible to achieve space saving also at a cable wire through which an image pickup unit is controlled and a signal is received from the image pickup unit. Thus, it is possible to incorporate a high-performance image pickup apparatus in a case of a system or arrangement in which an image pickup unit disposed in a small space is disposed separately from a control circuit that controls the image pickup unit. Specifically, since a large number of image pickup units are mounted on an automobile for which image pickup needs to be performed at various places outside and inside the automobile without blind spots, size reduction including size reduction of wires as in the present application is important, and thus it is easy to perform designing for incorporation with the present invention. The present invention is also applicable to a portable terminal for which size and weight reduction is required to achieve its portability, a network terminal such as an artificial intelligence (AI) speaker for which a smaller installation place is desired, an IoT (Internet of Things) home electronics, and a monitoring camera that monitors daily life to assure safety of a target. Moreover, it is possible to configure an image pickup unit that can be easily incorporated in a movable object such as a robot (including a vacuum cleaner) or a drone for which a movement function is important and thus size reduction, weight reduction, instrument barycenter, and balance are important.

Each above-described mount table is produced by the MID technology with injection molding in the above examples, but may be produced by another method. For example, such a mount table may be produced by fabrication with a 3D printer or by machining fabrication. The material of each mount table is not limited to resin but may be ceramic or glass epoxy.

What is claimed is:

1. An electronic module comprising:
   a mount body comprising:
      a first protrusion protruding from a first surface, the first protrusion having a first electrode mounting surface; and
      a second protrusion protruding from the first surface, the second protrusion having a second electrode mounting surface, the first and second protrusions having first and second side surfaces, respectively, the first and second protrusions and the first surface defining a concavity, with the first surface connecting the first and second side walls; and
   a land disposed on one or more of the first electrode mounting surface and the second electrode mounting surface, the land including an extending surface extending only partially between the one or more of the first electrode mounting surface and the second electrode mounting surface and the first surface.

2. The electronic module according to claim 1, wherein the extending surface extending only partially between the first electrode mounting surface and the first surface.

3. The electronic module according to claim 1, wherein the land comprises a first land provided on the first mounting surface and a second land provided on the second mounting surface, and
   further comprising:
      a component having an electrode corresponding to one or more of the first land and the second land; and
      solder electrically connecting one or more of the first land second land to a corresponding electrode, wherein the solder does not electrically connect with an other of the first land and the second land.

4. The electronic module according to claim 1, wherein the mount body further comprises a third protrusion protruding from the first surface to support an electronic component electrically connected to the land disposed on one or more of the first electrode mounting surface and the second electrode mounting surface; and
   the third protrusion having a greater height from the first surface than the first and second protrusion having the land.

5. The electronic module according to claim 1, wherein the concavity is a groove formed in the mount body.

6. The electronic module according to claim 1, wherein the concavity is a through-hole penetrating the mount body.

7. The electronic module according to claim 1, further comprising:
   a component provided on the first electrode mounting surface,
   wherein the first protrusion has a first height from the first surface,
   the component has a second height from the first surface, the second height is smaller than the first height.

8. The electronic module according to claim 3, further comprising:
   a third protrusion protruding from the first surface,
   wherein the third protrusion is provided on the first surface.

9. The electronic module according to claim 1, wherein the mount body further includes a plurality of via holes each penetrating from the one or more of the first electrode mounting surface and the second electrode mounting surface to a second surface, the second surface being farther from the one or more of the first electrode mounting surface and the second electrode mounting surface than the first surface.

10. The electronic module according to claim 9, wherein the mount body further includes a plurality of wiring patterns connected to the plurality of via holes at the second surface.

11. The electronic module according to claim 9, wherein one or more of the plurality of vias holes has a first opening on the one or more of the first electrode mounting surface and the second electrode mounting surface and a second opening on the second surface, the first opening is smaller than the second opening.

12. An image pickup unit comprising:
   an image pickup device;
   a mount body comprising:
      a first protrusion protruding from a first surface, the first protrusion having a first electrode mounting surface; and
      a second protrusion protruding from the first surface, the second protrusion having a second electrode mounting surface, the first and second protrusions having first and second side surfaces, respectively, the first and second protrusions and the first surface defining a concavity, with the first surface connecting the first and second side walls; and
   a land disposed on one or more of the first electrode mounting surface and the second electrode mounting surface, the land including an extending surface extending only partially between the one or more of the first electrode mounting surface and the second electrode mounting surface and the first surface.

13. An endoscope comprising:
   an insertion portion;
   the electronic module according to claim 1, the electronic module provided at the insertion portion; and
   an image pickup module provided at the insertion portion, the image pickup module comprises an image pickup device and an optical system.

14. The electronic module according to claim 1, further comprising:
   a component having an electrode corresponding to one or more of the first land and the second land; and
   solder electrically connecting one or more of the first land second land to a corresponding electrode;
   wherein the solder covers a portion of the land and a portion of one or more of the first side surface or the second side surface.

15. The electronic module according to claim 1, wherein a first portion of the land corresponding to the one or more of the first electrode mounting surface and the second electrode mounting surface has a first thickness and a second portion of the land corresponding to the extending surface has a second thickness larger than the first thickness.

16. The electronic module according to claim 1, wherein the land has a first length and a second length, smaller than the first length, extending in a direction from the one or more of the first electrode mounting surface and the second electrode mounting surface toward the first surface.

17. The electronic module according to claim 16, wherein the first length is provided at an opposite side relative to the concavity.

18. The electronic module according to claim 16, wherein the first length is provided at an opposite side relative to the second protrusion.

19. The electronic module according to claim 1, further comprising a plurality of a third protrusions protruding from the first surface, the plurality of a third protrusion are provided to surround the first protrusion and the second protrusion.

20. The electronic module according to claim 1, wherein the concavity has a cross shape when viewed in a direction from the one or more of the first electrode mounting surface and the second electrode mounting surface toward the first surface.

* * * * *